US012201820B2

(12) United States Patent
Brown

(10) Patent No.: US 12,201,820 B2
(45) Date of Patent: Jan. 21, 2025

(54) VENTRICULAR ASSIST DEVICE AND CARDIAC ELECTRICAL STIMULATION SYSTEM FOR THERAPY CONTROL

(71) Applicant: Medtronic, Inc., Minneapolis, MN (US)

(72) Inventor: Mark L. Brown, North Oaks, MN (US)

(73) Assignee: Medtronic, Inc., Minneapolis, MN (US)

(*) Notice: Subject to any disclaimer, the term of this patent is extended or adjusted under 35 U.S.C. 154(b) by 511 days.

(21) Appl. No.: 17/542,032

(22) Filed: Dec. 3, 2021

(65) Prior Publication Data

US 2022/0088366 A1 Mar. 24, 2022

Related U.S. Application Data

(62) Division of application No. 16/296,863, filed on Mar. 8, 2019, now Pat. No. 11,213,670.

(Continued)

(51) Int. Cl.
*A61M 60/148* (2021.01)
*A61B 5/00* (2006.01)
*A61B 5/363* (2021.01)
*A61M 60/178* (2021.01)
*A61M 60/216* (2021.01)
*A61M 60/422* (2021.01)
(Continued)

(52) U.S. Cl.
CPC ......... *A61M 60/148* (2021.01); *A61B 5/4836* (2013.01); *A61M 60/178* (2021.01); *A61M 60/216* (2021.01); *A61M 60/422* (2021.01); *A61M 60/515* (2021.01); *A61M 60/82* (2021.01); *A61M 60/824* (2021.01); *A61M 60/857* (2021.01); *A61N 1/3627* (2013.01); *A61N 1/36514* (2013.01); *A61N 1/3754* (2013.01); *A61N 1/3904* (2017.08); *A61N 1/3956* (2013.01); *A61N 1/3962* (2013.01); *A61B 5/363* (2021.01); *A61N 1/37288* (2013.01); *A61N 1/37512* (2017.08); *A61N 1/3925* (2013.01)

(58) Field of Classification Search
None
See application file for complete search history.

(56) References Cited

U.S. PATENT DOCUMENTS 7,761,150 B2 7/2010 Ghanem et al.
7,976,271 B2 7/2011 LaRose et al.
(Continued)

FOREIGN PATENT DOCUMENTS

CN 107072581 A 8/2017
CN 107073274 A 8/2017
EP 2570142 A1 3/2013

OTHER PUBLICATIONS

"Office Action Issued in Chinese Patent Application No. 201980017953.X", Mailed Date: Jan. 13, 2024, 19 Pages.
(Continued)

*Primary Examiner* — Amanda K Hulbert
*Assistant Examiner* — Philip C Edwards

(57) ABSTRACT

A medical device system includes a cardiac electrical stimulation device and a ventricular assist device (VAD). The cardiac stimulation device and the VAD are capable of communication with each other to confirm detection of cardiac events.

18 Claims, 8 Drawing Sheets

Related U.S. Application Data

(60) Provisional application No. 62/640,834, filed on Mar. 9, 2018.

(51) Int. Cl.

| | | |
|---|---|---|
| *A61M 60/515* | (2021.01) | |
| *A61M 60/82* | (2021.01) | |
| *A61M 60/824* | (2021.01) | |
| *A61M 60/857* | (2021.01) | |
| *A61N 1/362* | (2006.01) | |
| *A61N 1/365* | (2006.01) | |
| *A61N 1/372* | (2006.01) | |
| *A61N 1/375* | (2006.01) | |
| *A61N 1/39* | (2006.01) | |

(56) References Cited

U.S. PATENT DOCUMENTS

| | | |
|---|---|---|
| 7,991,467 B2 | 8/2011 | Markowitz et al. |
| 8,961,390 B2 | 2/2015 | LaRose et al. |
| 9,433,714 B2 | 9/2016 | Voskoboynikov et al. |
| 9,504,843 B2 | 11/2016 | Frustaci et al. |
| 9,592,327 B2 | 3/2017 | Wariar et al. |
| 9,855,414 B2 | 1/2018 | Marshall et al. |
| 2002/0177878 A1 | 11/2002 | Poore et al. |
| 2004/0172075 A1 | 9/2004 | Shafer et al. |
| 2004/0172077 A1 | 9/2004 | Chinchoy |
| 2011/0178361 A1* | 7/2011 | Yomtov .............. A61M 60/216 600/16 |
| 2011/0270331 A1* | 11/2011 | Peters .................. A61N 1/3627 607/3 |
| 2012/0059459 A1 | 3/2012 | Asirvatham et al. |
| 2015/0051438 A1 | 2/2015 | Taskin |
| 2015/0073203 A1 | 3/2015 | Wariar et al. |
| 2015/0306375 A1 | 10/2015 | Marshall et al. |
| 2016/0158567 A1 | 6/2016 | Marshall et al. |
| 2016/0175603 A1 | 6/2016 | Sheldon et al. |
| 2017/0119256 A1* | 5/2017 | Demou ............... A61M 60/216 |
| 2017/0197028 A1 | 7/2017 | Goldsmith |
| 2017/0312532 A1 | 11/2017 | Zhang et al. |
| 2017/0354827 A1 | 12/2017 | Zhang et al. |

OTHER PUBLICATIONS

Cantillon et al., "Improved Survival Among Ventricular Assist Device Recipients with a Concomitant Implantable Cardioverter-Defibrillator", Heart Rhythm, 2009, 6 pages.

(PCT/US2019/021391) PCT Notification of Transmittal of the International Search Report and the Written Opinion of the International Searching Authority, Mailed Jul. 19, 2019, 17 pages.

Cantillon et al., Low Cardiac Output Associated With Ventricular Tachyarrhythmias in Continuous-Flow LVAD 1 Recipients with a Concomitant ICD (Loco VT Study), The Journal of Heart and Lung Transplantation, vol. 33, No. 3, Mar. 2014, 3 pages.

Refaat et al., "Survival Benefit of Implantable Cardioverter-Defibrillators in Left Ventricular Assist Device-Supported Heart Failure Patients", Journal of Cardiac Failure, vol. 18, No. 2, 2012, 6 pages.

* cited by examiner

VENTRICULAR ASSIST DEVICE AND CARDIAC ELECTRICAL STIMULATION SYSTEM FOR THERAPY CONTROL

CROSS REFERENCE TO RELATED APPLICATIONS

This application is a Divisional of U.S. patent application Ser. No. 16/296,863, filed on Mar. 8, 2019, which claims the benefit of the filing date of provisional U.S. Patent Application No. 62/640,834, filed Mar. 9, 2018, the content of both of which is incorporated herein by reference in its entirety.

TECHNICAL FIELD

This disclosure relates to a medical device system including a ventricular assist device (VAD) and a cardiac device configured to cooperatively monitor a patient and/or control therapies delivered to the patient.

BACKGROUND

A VAD is an implantable blood pump that assists an impaired heart by pumping blood to support the workload of the heart. A VAD may be coupled along the arterial system, e.g., between a ventricular chamber and the aorta or another artery, to pump blood from the ventricle into the arterial system. Such assistance can be provided to a heart failure patient acutely or chronically, as a bridge to heart transplant, as temporary support to allow myocardial recovery, or as a permanent assist device for heart failure patients contraindicated for heart transplant.

A cardiac electrical stimulation device, such as an implantable cardioverter-defibrillator (ICD), wearable cardiac defibrillator (WCD) or other cardiac defibrillation device, monitors a patient's heart rhythm and provides electrical stimulation therapy, such as bradycardia pacing, anti-tachycardia pacing or a cardioversion defibrillation shock, in response to detecting an abnormal electrical rhythm. Heart failure patients are at risk of sudden cardiac death due to arrhythmia. ICD implantation or prescription of a WCD in heart failure patients reduces the risk of sudden cardiac death. Patients having both a VAD and a cardiac defibrillation device may have improved survival.

SUMMARY

The techniques of this disclosure generally relate to a medical device system including a cardiac device capable of monitoring and/or providing therapy, such as an ICD or WCD, and a VAD. A system including an ICD and the VAD operating according to the techniques disclosed herein cooperatively provide cardiac monitoring and control therapy delivered to the patient. The cardiac stimulation device and the VAD are capable of communication. Each device monitors one or more signals received by the respective cardiac stimulation device or VAD for detecting cardiac events. In response to one of the cardiac stimulation device or VAD detecting a cardiac event, a signal is transmitted to the other one of the cardiac stimulation device and VAD for requesting a confirmation of the detected cardiac event or alerting the other device that the cardiac event is suspected. Based on cardiac event detection and the communication signals transmitted between the cardiac stimulation device and the VAD, each of the cardiac stimulation device and the VAD may select an appropriate response to a detected cardiac event, which may include generating an alert, storing the cardiac event data in memory for review by a clinician, and/or delaying, adjusting or delivering a therapy to alleviate or terminate the cardiac event.

In one example, the disclosure provides a device comprising a sensing circuit configured to receive a cardiac electrical signal, a therapy delivery circuit configured to deliver an electrical stimulation therapy, a telemetry circuit configured for communication with a ventricular assist device (VAD), and a control circuit coupled to the sensing circuit, the therapy delivery circuit and the telemetry circuit. The control circuit is configured to detect a cardiac event from the cardiac electrical signal received by the sensing circuit, receive a confirmation signal transmitted by the VAD, select a therapy delivery response based on the received confirmation signal and control the therapy delivery circuit according to the selected therapy delivery response.

In another example the disclosure provides a method comprising obtaining a cardiac electrical signal, detecting a cardiac event from the cardiac electrical signal, receiving a confirmation signal from a ventricular assist device (VAD), selecting a therapy delivery response based on the received confirmation signal, and controlling the therapy delivery circuit according to the selected therapy delivery response.

In yet another example the disclosure provides a system comprising a first device comprising a blood pump comprising a motor, an inflow cannula for receiving blood from a patient's heart, and a flow outlet for coupling to a patient's artery. The first device also includes a controller comprising a power source, a processor and a telemetry circuit configured for communication with a second device. The first device also includes a drive line coupled between the blood pump and the controller for transmitting a drive signal to the blood pump. The controller is configured to estimate a flow rate of the blood pump, detect a cardiac event from the estimated flow rate, and control the telemetry circuit to transmit a request signal to the second device in response to detecting the cardiac event.

In a further example, a method comprises estimating a flow rate of a blood pump, detecting a cardiac event from the estimated flow rate and transmitting a request signal to a second device in response to detecting the cardiac event.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

In general, this disclosure describes a medical device system including a VAD and another cardiac device and techniques for detecting a cardiac event and cooperatively managing monitoring or a therapy or other response to the detected cardiac event by the VAD and/or cardiac device. The cardiac device may be stimulation device such as an ICD, WCD, automated external defibrillator (AED) or other defibrillator device. In other examples, the cardiac device may be a monitoring device with no therapy capabilities, such as a cardiac monitor. The cardiac event may be a cardiac rhythm event, e.g., n tachyarrhythmia such as ventricular tachycardia (VT) or ventricular fibrillation (VF), which may initially be detected by the cardiac stimulation device. In other instances, the cardiac event may be a hemodynamic event, e.g., a low flow or suction event, which may be initially detected by the VAD. The cardiac stimulation device and the VAD are configured for communication for receiving data from the other device. The received data may be used in confirming, reclassifying or rejecting the detected cardiac event and/or selecting an appropriate response to the cardiac event detection, which may include generating a patient alert, delaying, withholding, adjusting or delivering a therapy, and/or storing and displaying cardiac event data for review by a clinician.

The techniques will be described with respect to a system including an ICD and VAD for illustrative purposes. However, the methods, systems and techniques of this disclosure may be used in other medical device systems that do not include an ICD or include another cardiac stimulation device in addition to the ICD, such as a WCDs, an AED, or the like.

Figure 1A:
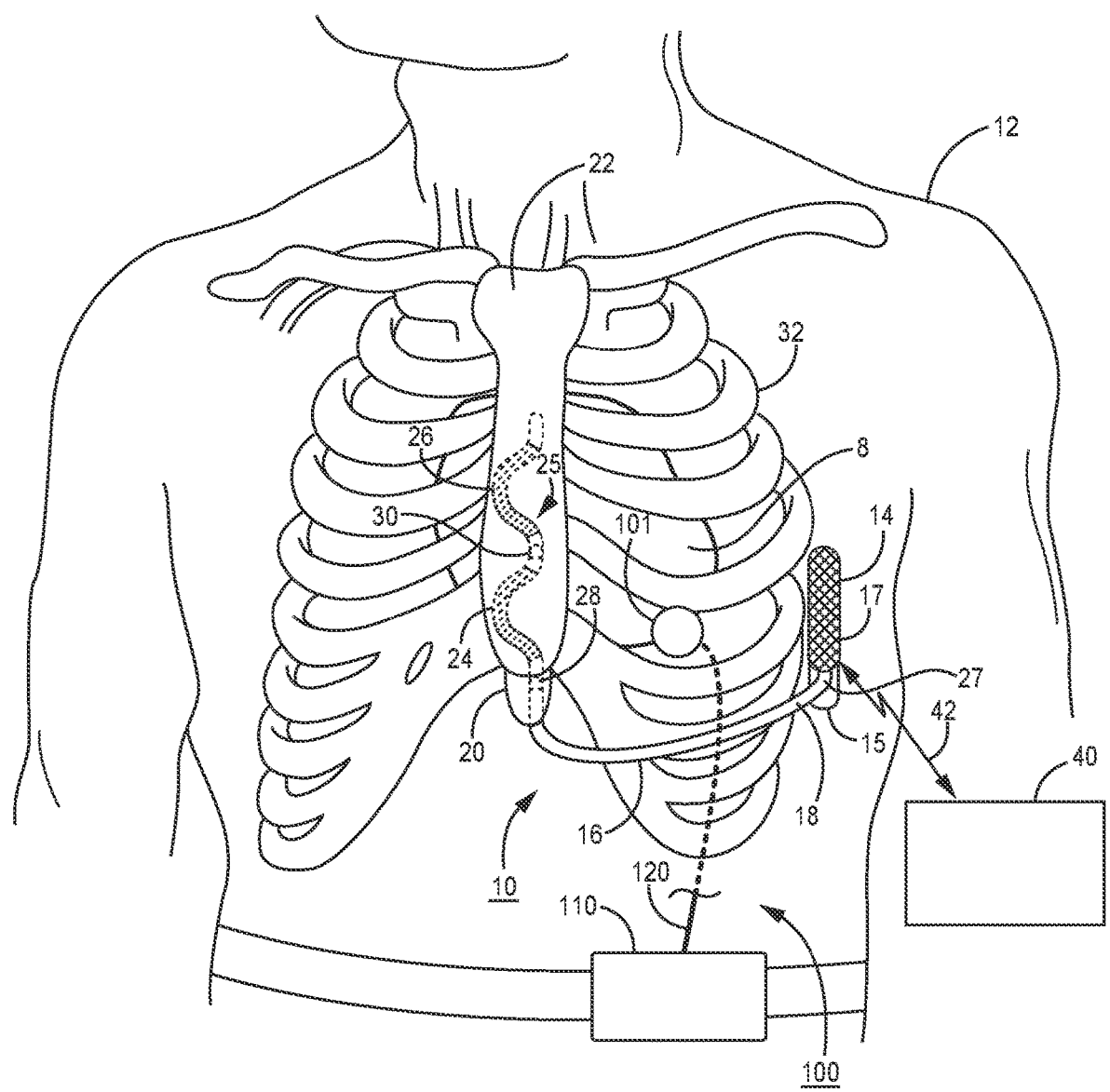
FIGS. 1A and 1B are conceptual diagrams of a medical device system including an ICD and a VAD coupled to a patient's heart according to one example.
Figure 1B:
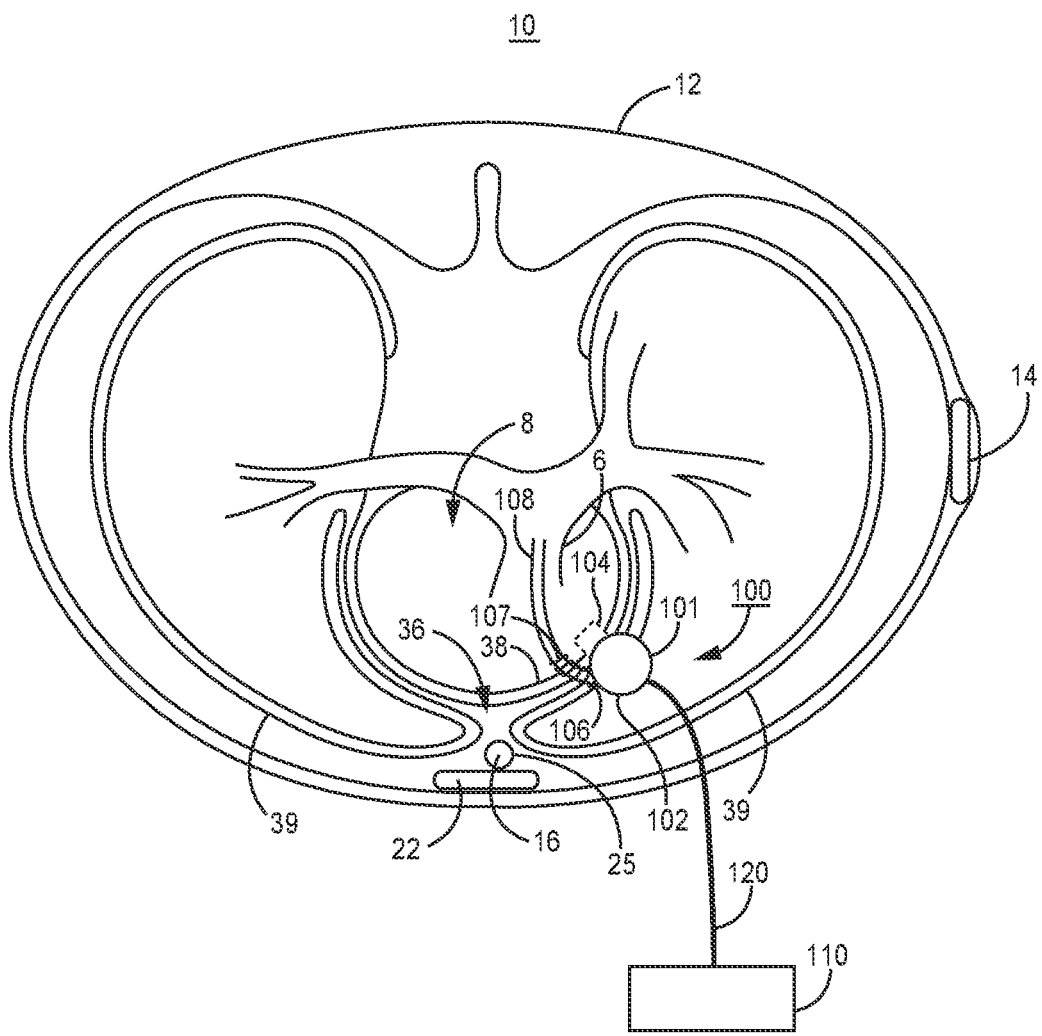

FIGS. 1A and 1B are conceptual diagrams of a medical device system 10 including an ICD 14 and a VAD 100 coupled to a patient's heart 8 according to one example. FIG. 1A is a front view of system 10 implanted within patient 12. FIG. 1B is a transverse view of system 10 implanted within patient 12. ICD 14 is coupled to an extra-cardiovascular lead 16 carrying one or more electrodes for sensing cardiac electrical signals and for delivering cardiac electrical stimulation therapies. VAD 100 is shown as an implantable blood pump 101 which is fluidly coupled between a heart ventricle and an artery of patient 12. Blood pump 101 is electrically coupled to an external, wearable controller 110 via a percutaneous drive line 120.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). Housing 15 may be used as an active can electrode for use in delivering cardioversion/defibrillation (CV/DF) shocks or other high voltage pulses delivered using a high voltage therapy circuit. In other examples, housing 15 may be available for use in delivering unipolar, low voltage cardiac pacing pulses and/or for sensing cardiac electrical signals in combination with electrodes carried by lead 16. In other instances, the housing 15 of ICD 14 may include a plurality of electrodes on an outer portion of the housing. The outer portion(s) of the housing 15 functioning as an electrode(s) may be coated with a material, such as titanium nitride, e.g., for reducing post-stimulation polarization artifact.

ICD 14 is connected to an extra-cardiovascular electrical stimulation and sensing lead 16. ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, cardiac electrical signal sensing circuitry, therapy delivery circuitry, power sources and other components for sensing cardiac electrical signals, detecting a heart rhythm, controlling and delivering electrical stimulation pulses to treat an abnormal heart rhythm, and for communicating with VAD 100 and an external programmer 40.

Elongated lead body 18 has a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently.

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, electrodes 24 and 26 may be used in a sensing vector used to sense cardiac electrical signals and detect and discriminate cardiac arrhythmias.

Electrodes 28 and 30 are relatively smaller surface area electrodes which are available for use in sensing electrode vectors for sensing cardiac electrical signals and may be used for delivering relatively low voltage pacing pulses in some configurations. Electrodes 28 and 30 are referred to as pace/sense electrodes because they are generally configured for use in low voltage applications, e.g., used as either a cathode or anode for delivery of pacing pulses and/or sensing of cardiac electrical signals, as opposed to delivering high voltage cardioversion defibrillation shocks. In some instances, electrodes 28 and 30 may provide only pacing functionality, only sensing functionality or both.

ICD 14 may obtain cardiac electrical signals corresponding to electrical activity of heart 8 via one or more sensing vectors that include combinations of electrodes 24, 26, 28 and/or 30. In some examples, housing 15 of ICD 14 is used in combination with one or more of electrodes 24, 26, 28 and/or 30 in a sensing electrode vector. In one example, a sensing vector includes electrodes 28 and 30. In another example, a sensing vector includes defibrillation electrode 24 and housing 15. These examples are illustrative in nature and not intended as limiting. Various sensing electrode vectors utilizing combinations of electrodes 24, 26, 28, and 30 and housing 15 may be used for acquiring one or more cardiac electrical signals received by sensing circuitry included in ICD 14.

In the example illustrated in FIGS. 1A and 1B, electrode 28 is located proximal to defibrillation electrode 24, and electrode 30 is located between defibrillation electrodes 24 and 26. Lead 16 may include none, one, two or more pace/sense electrodes, which, when present, may be carried at other locations along lead body 18 than the particular locations shown. Electrodes 28 and 30 are illustrated as ring electrodes but may comprise any of a number of different types of electrodes, including ring electrodes, short coil electrodes, hemispherical electrodes, directional electrodes, segmented electrodes, or the like.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18 are each electrically coupled with respective defibrillation electrodes 24 and 26 and pace/sense electrodes 28 and 30, which may be separate respective insulated conductors within the lead body 18. The respective conductors electrically couple the electrodes 24, 26, 28, and 30 to circuitry, such as a therapy delivery circuit and/or a sensing circuit, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28 and 30 and transmit sensed electrical signals from one or more of defibrillation electrodes 24 and 26 and/or pace/sense electrodes 28 and 30 to the sensing circuit within ICD 14.

The lead body 18 of lead 16 may be formed from a non-conductive material, including silicone, polyurethane, fluoropolymers, mixtures thereof, and other appropriate materials, and shaped to form one or more lumens within which the one or more conductors extend. Lead body 18 may be tubular or cylindrical in shape. In other examples, the distal portion 25 (or all of) the elongated lead body 18 may have a flat, ribbon or paddle shape. Lead body 18 may be formed having a preformed distal portion 25 that is generally straight, curving, bending, serpentine, undulating or zig-zagging.

In the example shown, lead body 18 includes a curving distal portion 25 having two "C" shaped curves, which together may resemble the Greek letter epsilon, "ε." Defibrillation electrodes 24 and 26 are each carried by one of the two respective C-shaped portions of the lead body distal portion 25. The two C-shaped curves are seen to extend or curve in the same direction away from a central axis of lead body 18, along which pace/sense electrodes 28 and 30 are positioned. Pace/sense electrodes 28 and 30 may, in some instances, be approximately aligned with the central axis of the straight, proximal portion of lead body 18 such that mid-points of defibrillation electrodes 24 and 26 are laterally offset from pace/sense electrodes 28 and 30.

Other examples of extra-cardiovascular leads including one or more defibrillation electrodes and one or more pacing and sensing electrodes carried by curving, serpentine, undulating or zig-zagging distal portion of the lead body 18 that may be implemented with the techniques described herein are generally disclosed in pending U.S. Pat. Publication No. 2016/0158567 (Marshall, et al.), incorporated herein by reference in its entirety. The techniques disclosed herein are not limited to any particular lead body design, however. In other examples, lead body 18 is a flexible elongated lead body without any pre-formed shape, bends or curves. Various example configurations of extra-cardiovascular leads and electrodes and dimensions that may be implemented in conjunction with the therapy management techniques disclosed herein are described in pending U.S. Publication No. 2015/0306375 (Marshall, et al.) and U.S. Pat. No. 9,855,414 (Marshall, et al.), both of which are incorporated herein by reference in their entirety.

Lead 16 is shown to extend medially from the connector assembly 27 of ICD 14, subcutaneously or submuscularly over the ribcage 32 toward a center of the torso of patient 12, e.g., toward xiphoid process 20. At a location near xiphoid process 20, lead 16 bends or turns and extends superiorly and substernally under the ribcage and/or sternum, substantially parallel to sternum 22. Anterior mediastinum 36 (see FIG. 1B) may be viewed as being bounded laterally by pleurae 39, posteriorly by pericardium 38, and anteriorly by sternum 22 (see FIG. 1B). The distal portion 25 of lead 16 may extend along the posterior side of sternum 22 substantially within the loose connective tissue and/or substernal musculature of anterior mediastinum 36. A lead implanted such that the distal portion 25 is substantially within anterior mediastinum 36, may be referred to as a "substernal lead."

In the example illustrated in FIGS. 1A and 1B, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to the pericardium 38 of heart 8.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. The path of extra-cardiovascular lead 16 may depend on the location of ICD 14, the arrangement and position of electrodes carried by the lead body 18, the location of VAD 100, and/or other factors.

ICD 14 analyzes the cardiac electrical signals received from one or more sensing electrode vectors to monitor for abnormal rhythms, such as bradycardia, supraventricular tachycardia (SVT), VT and VF. ICD 14 may analyze the heart rate and morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated herein by reference in its entirety. A variety of arrhythmia detection algorithms may be implemented in ICD 14, included in system 10 comprising VAD 100, for use in initially detecting a cardiac event as an abnormal heart rhythm or for determining if a cardiac electrical event is occurring in response to receiving a request from VAD 100.

ICD 14 may generate and deliver electrical stimulation therapy in response to detecting a tachyarrhythmia (e.g., VT or VF) using a therapy delivery electrode vector which may be selected from any of the available electrodes 24, 26, 28 30 and/or housing 15. ICD 14 may deliver ATP in response to VT detection, and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses or bradycardia pacing pulses using a pacing electrode vector that includes one or more of the electrodes 24, 26, 28, and 30 and the housing 15 of ICD 14.

An external programmer 40 is shown in telemetric communication with ICD 14 by a communication link 42. External programmer 40 may include a processor, display, user interface, telemetry unit and other components for communicating with ICD 14 for transmitting and receiving data via communication link 42. Communication link 42 may be established between ICD 14 and external programmer 40 using a radio frequency (RF) link such as BLUETOOTH®, Wi-Fi, or Medical Implant Communication Service (MICS) or other RF or communication frequency bandwidth.

External programmer 40 may be embodied as a programmer used in a hospital, clinic or physician's office to retrieve data from ICD 14 and to program operating parameters and algorithms in ICD 14 for controlling ICD functions. External programmer 40 may alternatively be embodied as a home monitor or hand held device. External programmer 40 may be used to program cardiac sensing parameters (e.g., R-wave sensing parameters), cardiac rhythm detection parameters, and therapy control parameters used by ICD 14. Data stored or acquired by ICD 14, including physiological signals or associated data derived therefrom, results of device diagnostics, and histories of detected rhythm episodes and delivered therapies, may be retrieved from ICD 14 by external programmer 40 following an interrogation command. Logs of communication signals with VAD 100 may be retrieved by programmer 40, along with related therapy delivery or other responses performed by ICD 14 to the communication signals received from VAD 100.

VAD 100 may include a blood pump 101 configured as a centrifugal, rotary blood pump having a pump housing 102 enclosing an interior pump chamber and rotary impeller in one example. Blood pump 101 is shown coupled between the patient's heart 8 and an artery, as best seen in FIG. 1B. For example, blood pump 101 may be coupled between the left ventricle (LV) and the ascending aorta 6 to pump blood in parallel with the LV into the arterial system. The interior pump chamber (shown in FIG. 4) is in fluid communication with an inflow cannula 104 that may be inserted into the LV, e.g. via a sewing ring, for receiving blood from the patient's heart 8. At least a portion of the exterior circumferential surface of inflow cannula 104 may be sintered to promote tissue adhesions between the ventricular myocardium and inflow cannula 104. Pump housing 102 may have a relatively low profile, e.g., an overall height of 30 mm or less, so that pump housing 102 may be implanted within the pericardial space in some examples. To accommodate implantation within the pericardial space, inflow cannula 104 may be relatively short, e.g., 60 mm or less.

The interior of the pump housing 102 is also in fluid communication with a flow outlet 106 that is coupled to an outflow vascular graft 108. Graft 108 is anastomosed to the ascending aorta 6 (or other artery) to direct the pump outflow into the patient's arterial system. In some examples, graft 108 may be an 8 to 12 mm diameter graft fabricated from a polyester material. Graft 108 may include a strain relief member 107 to prevent kinking of vascular graft 108. Strain relief member 107 may extend from flow outlet 106 exteriorly along at least a portion of the length of vascular graft 108. Strain relief member 107 may be formed of a coiled metal or plastic material that provides flexibility of the proximal portion of vascular graft 108 but resists kinking.

Controller 110 may be a wearable device that includes one or more rechargeable batteries and/or power supply connections (e.g., an AC power supply connection) to provide power to the controller 110. In the examples described below in conjunction with FIGS. 4 and 5, motor stators included in blood pump 101 receive a drive current from controller 110 via percutaneous drive line 120. VAD 100 may be a continuous flow pump and may have a constant or variable speed, such as the pump generally disclosed in U.S. Pat. No. 9,433,714 (Voskoboynikov et al.), incorporated herein by reference in its entirety.

VAD 100 and ICD 14 are configured for communication with one another, either bidirectional or unidirectional, for managing therapy delivery. Communication may be established using a wireless RF communication link established between RF transceivers included in each of VAD 100 and ICD 14. The techniques disclosed herein are not limited to use with a particular communication method or protocol, however, and other communication methods besides RF wireless telemetry may be used, including intrabody tissue conduction communication, inductive communication, and the like. As described below, communication between VAD 100 and ICD 14 may be performed to confirm an arrhythmia detected by ICD 14, confirm a suction event detected by VAD 100, or warn ICD 14 to anticipate a shockable rhythm. A shockable rhythm is a tachyarrhythmia that is to be treated by delivery of a cardioversion/defibrillation shock, such VT or VF. In some instances, a shockable rhythm detection may be a false detection due to oversensing of T-waves, electromagnetic interference, or other non-cardiac noise in the cardiac electrical signal. A false shockable rhythm detection may lead to an unnecessary CV/DF shock, which is painful to the patient. In some examples, ICD 14 may request a confirmation from VAD 100 that a low flow condition exists for confirming a shockable rhythm initially detected by ICD 14 based on cardiac electrical signals received and monitored by ICD 14. Other examples of cooperative patient monitoring and therapy delivery control that may be performed by system 10 are described below.

FIGS. 1A and 1B are illustrative in nature and should not be considered limiting of the practice of the techniques disclosed herein. For example, the implant locations of ICD 14, lead 16 and blood pump 101 may be different than the particular locations shown in FIGS. 1A and 1B. Furthermore, other ICD and lead systems and/or other VAD systems may be substituted for the example ICD 14 and VAD 100 shown in system 10 and configured to perform the techniques disclosed herein.

Figure 2:
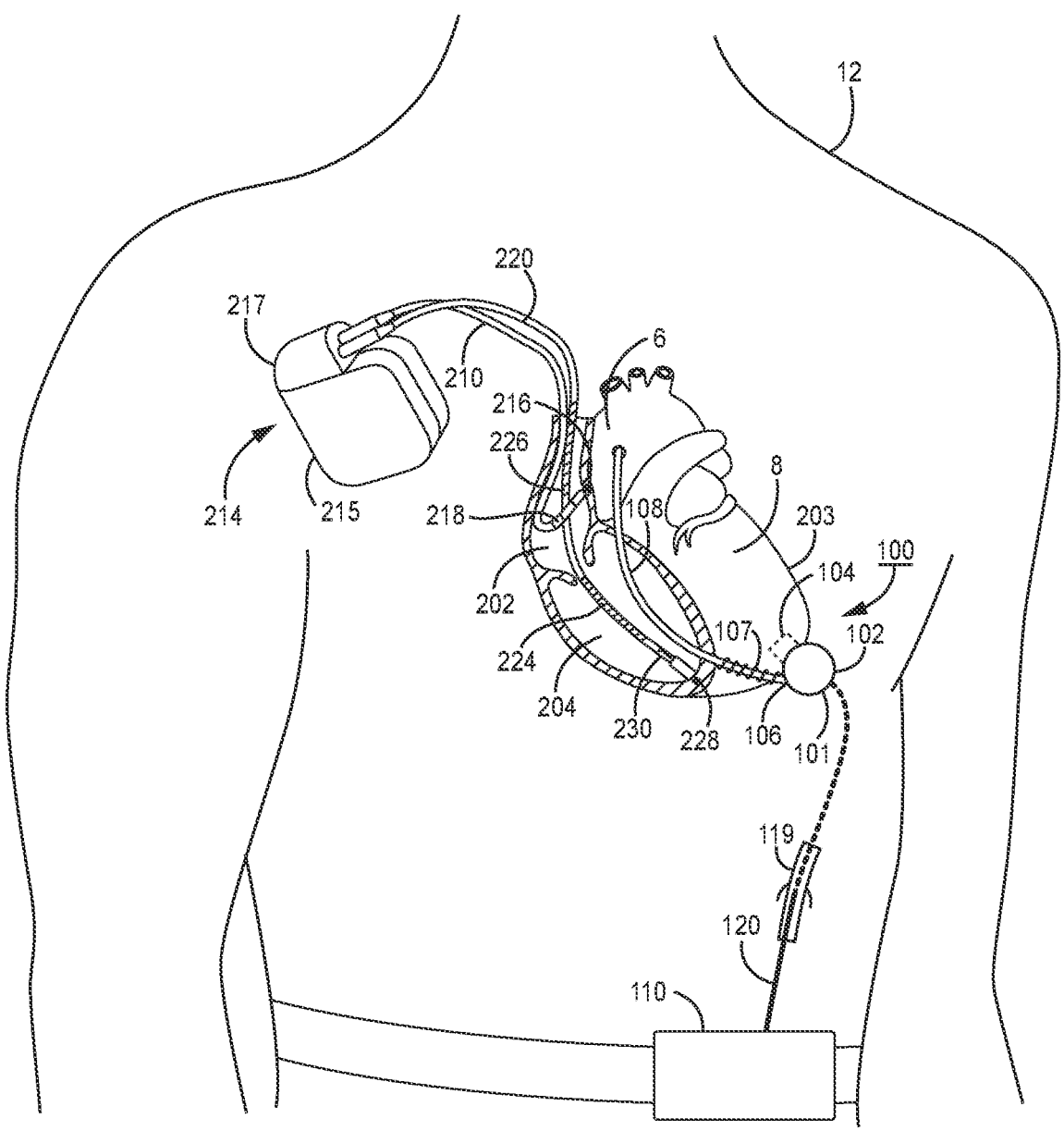
FIG. 2 is a conceptual diagram of a patient implanted with an medical device system including an ICD and VAD according to another example.

FIG. 2 is a conceptual diagram of patient 12 implanted with a medical device system 200 including an ICD 214 and VAD 100 according to another example. In this example, ICD 214 is coupled to transvenous leads carrying electrodes for sensing cardiac electrical signals and delivering electrical stimulation pulses to heart 8 for cardiac rhythm management, such as bradycardia pacing, ATP cardiac resynchronization therapy (CRT) and/or CV/DF shocks. ICD 214 is shown implanted in a right pectoral position in FIG. 2; however it is recognized that ICD 214 may be implanted in a left pectoral position, particularly when ICD 214 includes cardioversion and defibrillation capabilities using housing 215 as an electrode.

ICD 214 is illustrated as a dual chamber device for sensing and therapy delivery in an atrial chamber 202 and a ventricular chamber 204 of heart 8. As such, ICD 214 includes connector assembly 217 having two connector bores for receiving proximal connectors of a right atrial (RA) lead 210 and a right ventricular (RV) lead 220. In other examples ICD 214 may be a single chamber device, e.g., connectable only to RV lead 220, or a multi-chamber device including a third connector bore, e.g., for receiving a coronary sinus lead to enable ICD 214 to sense left ventricular signals and deliver electrical stimulation pulses to the LV 203.

RA lead 210 may carry a distal tip electrode 216 and ring electrode 218 spaced proximal from the tip electrode 216 for delivering pacing pulses to the RA 202 and obtaining atrial electrical signals for producing an atrial intra-cardiac electrogram (EGM) signal by ICD 214. RV lead 220 may carry pacing and sensing electrodes 228 and 230 for delivering RV pacing pulses to the RV 204 and obtaining ventricular electrical signals for producing an RV EGM signal by ICD 214. RV lead 220 may also carry RV defibrillation electrode 224 and a superior vena cava (SVC) defibrillation electrode 226. Defibrillation electrodes 224 and 226 are shown as coil electrodes spaced apart proximally from the distal pacing and sensing electrodes 228 and 230.

ICD housing 215 encloses circuitry, as further described below, configured to detect arrhythmias and provide electrical stimulation therapy, such as bradycardia pacing, post-shock pacing, ATP, CRT and/or CV/DF shock therapy, using the electrodes 216, 218, 224, 226, 228 and 230 of transvenous leads 210 and 220. ICD 214 is configured to communicate with VAD 100 for the purposes of cooperatively monitoring patient 12 for cardiac events and managing therapy delivery.

As described in conjunction with FIGS. 1A and 1B, VAD 100 includes blood pump 101 having a pump housing 102 that encloses an interior pump chamber for receiving blood through inflow cannula 104 from the left ventricle 203 of heart 8. Pump housing 102 encloses a rotary impeller motor that drives blood through the interior pump chamber and out of flow outlet 106, through vascular graft 108, and into the ascending aorta 6. The percutaneous drive line 120 provides power and control signals from external controller 110, wearable by patient 12, to electromagnetic stators of the motor. Drive line 120 may include an exterior, circumferential sheath 119 of woven polyester or other biocompatible woven or porous material to promote tissue in-growth at the skin exit site of percutaneous drive line 120.

Figure 3:
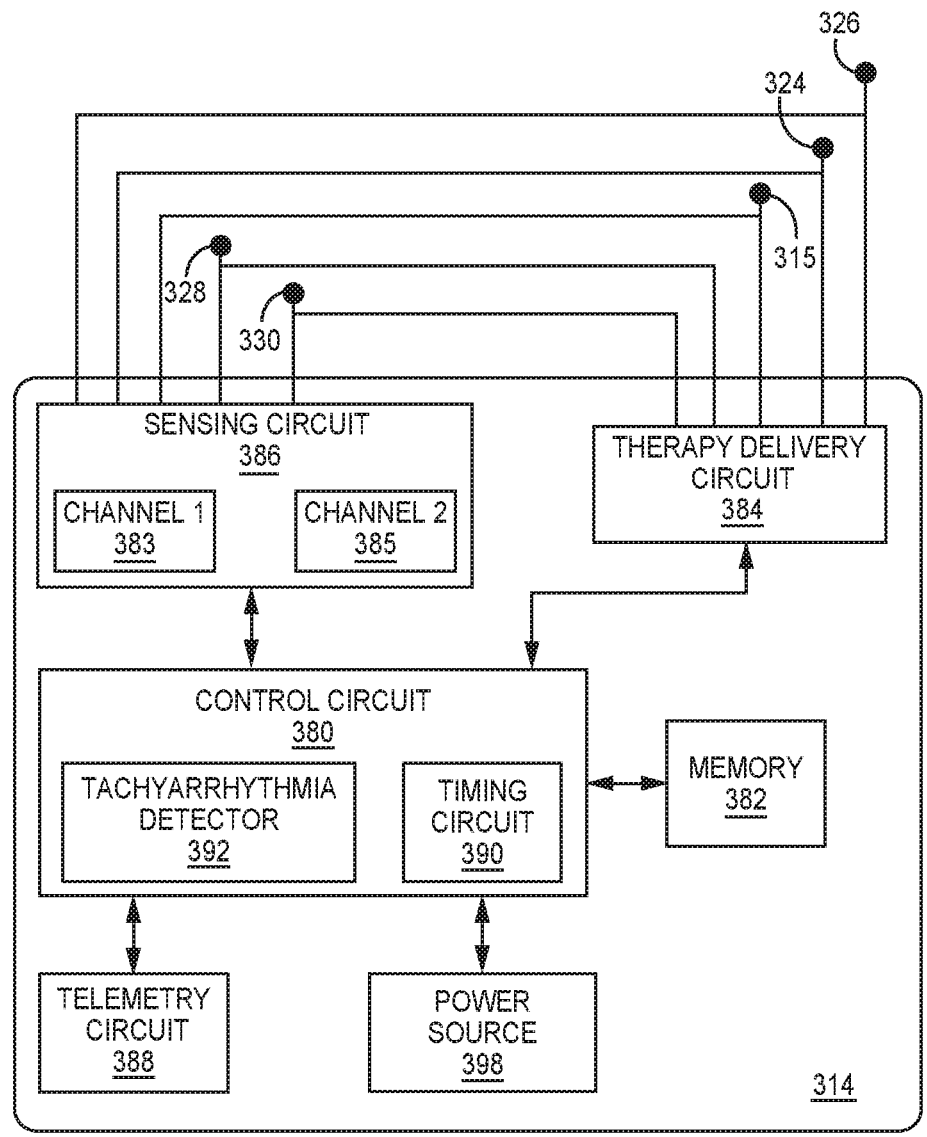
FIG. 3 is a schematic diagram of an ICD that may be co-implanted with a VAD for cooperative patient monitoring and therapy management according to one example.

FIG. 3 is a schematic diagram of an ICD 314 that may be co-implanted with VAD 100 for cooperatively monitoring a patient and managing therapy delivery according to one example. The circuitry shown and described in FIG. 3 may correspond to circuitry included in ICD 14 of FIG. 1A or in ICD 214 of FIG. 2. The same or similar circuitry may be included within other cardiac stimulation devices, such as WCDs or AEDs. The electronic circuitry enclosed within housing 315 (shown schematically as an electrode in FIG. 3) includes software, firmware and hardware that cooperatively monitor cardiac electrical signals produced by the patient's heart, determine when an electrical stimulation therapy is necessary, and deliver therapies as needed according to programmed therapy delivery algorithms and control parameters. The software, firmware and hardware are configured to detect tachyarrhythmias and deliver anti-tachyarrhythmia therapy, e.g., detect ventricular tachyarrhythmias and determine when ATP and/or CV/DF shocks are required. ICD 314 is coupled to one or more leads carrying electrodes 324, 326, 328, and 330, e.g., an extra-cardiovascular lead such as lead 16 shown in FIG. 1A or transvenous leads such as leads 210 and 220 shown in FIG. 2, for delivering electrical stimulation pulses to the patient's heart and for sensing cardiac electrical signals.

ICD 314 includes a control circuit 380, memory 382, therapy delivery circuit 384, sensing circuit 386, and telemetry circuit 388. A power source 398 provides power to the circuitry of ICD 314, including each of the components 380, 382, 384, 386, and 388 as needed. Power source 398 may include one or more energy storage devices, such as one or more rechargeable or non-rechargeable batteries. The connections between power source 398 and each of the other components 380, 382, 384, 386 and 388 are to be understood from the general block diagram of FIG. 3, but are not shown for the sake of clarity. For example, power source 398 may be coupled to one or more charging circuits included in therapy delivery circuit 384 for charging holding capacitors included in therapy delivery circuit 384 that are discharged at appropriate times under the control of control circuit 380 for producing electrical pulses according to a therapy protocol, such as for bradycardia pacing, CRT, post-shock pacing, ATP and/or CV/DF shock pulses. Power source 398 may also be coupled to components of sensing circuit 386, such as sense amplifiers, analog-to-digital converters, switching circuitry, etc., telemetry circuit 388, and memory 382 to provide power as needed.

The functional blocks shown in FIG. 3 represent functionality included in an ICD configured to sense cardiac electrical signals, deliver cardiac electrical stimulation therapy, and communicate with VAD 100 for cooperatively managing therapy delivery and may include any discrete and/or integrated electronic circuit components that implement analog and/or digital circuits capable of producing the functions attributed to an ICD herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the ICD and by the particular detection and therapy delivery methodologies employed by the ICD.

Providing software, hardware, and/or firmware to accomplish the described functionality in the context of any modern medical device system, given the disclosure herein, is within the abilities of one of skill in the art.

Memory 382 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 382 may include non-transitory computer readable media storing instructions that, when executed by one or more processing circuits, cause control circuit 380 and/or other ICD components to perform various functions attributed to ICD 314 or those ICD components. The non-transitory computer-readable media storing the instructions may include any of the media listed above.

The functions attributed to ICD 314 herein may be embodied as one or more integrated circuits. Depiction of different features as circuits is intended to highlight different functional aspects and does not necessarily imply that such circuits must be realized by separate hardware or software components. Rather, functionality associated with one or more circuits may be performed by separate hardware, firmware or software components, or integrated within common hardware, firmware or software components. For example, cardiac event sensing and tachyarrhythmia detection operations may be performed cooperatively by sensing circuit 386 and control circuit 380 and may include operations implemented in a processor or other signal processing circuitry included in control circuit 380 executing instructions stored in memory 382 that produce control signals such as blanking and timing intervals and sensing threshold amplitude signals sent from control circuit 380 to sensing circuit 386.

Control circuit 380 communicates, e.g., via a data bus, with therapy delivery circuit 384 and sensing circuit 386. Therapy delivery circuit 384 and sensing circuit 386 are electrically coupled to electrodes 324, 326, 328, 330 and the housing 315, which may function as a common or ground electrode or as an active can electrode for delivering CV/DF shock pulses or cardiac pacing pulses. In the example of FIG. 2, additional atrial electrodes carried by a transvenous atrial lead may be coupled to sensing circuit 386 and therapy delivery circuit 384.

Sensing circuit 386 may be selectively coupled to electrodes 328, 330 and/or housing 315 in order to monitor electrical activity of the patient's heart. Sensing circuit 386 may additionally be selectively coupled to defibrillation electrodes 324 and/or 326 for use in a sensing electrode vector together or in combination with one or more of electrodes 328, 330 and/or housing 315. Sensing circuit 386 may be enabled to selectively receive cardiac electrical signals from at least two sensing electrode vectors from the available electrodes 324, 326, 328, 330, and housing 315. Two cardiac electrical signals from two different sensing electrode vectors may be received simultaneously by sensing circuit 386. The two sensing electrode vectors may include two different ventricular sensing electrode vectors each coupled to a respective sensing channel 383 and 385. In other examples, when an atrial sensing electrode vector is available, e.g., when RA lead 210 is present carrying atrial pacing and sensing electrodes 216 and 218 (as shown in FIG. 2), one sensing channel 383 may be an atrial sensing channel and one sensing channel 385 may be a ventricular sensing channel.

Sensing circuit 386 may monitor one or both or the cardiac electrical signals at a time for sensing signals attendant to the depolarization and repolarization of the heart, e.g., P-waves attendant to the depolarization of the atrial myocardium and/or R-waves attendant to the depolarization of the ventricular myocardium, and providing digitized cardiac signal waveforms for analysis by control circuit 380. For example, sensing circuit 386 may include switching circuitry (not shown) for selecting which of electrodes 324, 326, 328, 330, and housing 315 are coupled to a first sensing channel 383 and which are coupled to a second sensing channel 385 of sensing circuit 386. Switching circuitry may include a switch array, switch matrix, multiplexer, or any other type of switching device suitable to selectively couple components of sensing circuit 386 to selected electrodes.

Each sensing channel 383 and 385 may be configured to amplify, filter and digitize the cardiac electrical signal received from selected electrodes coupled to the respective sensing channel to improve the signal quality for detecting cardiac electrical signals, such as R-waves or performing other signal analysis. The cardiac detection circuitry within sensing circuit 386 may include one or more sense amplifiers, filters, rectifiers, threshold detectors, comparators, analog-to-digital converters (ADCs), timers or other analog or digital components. A cardiac sensing threshold may be automatically adjusted by sensing circuit 386 under the control of control circuit 380, based on timing intervals and sensing threshold values determined by control circuit 380, stored in memory 382, and/or controlled by hardware, firmware and/or software of control circuit 380 and/or sensing circuit 386.

Upon detecting a cardiac electrical signal (e.g., an R-wave or P-wave) based on a sensing threshold crossing the respective cardiac sensing threshold, sensing circuit 386 may produce an indication of the sensed signal, such as an R-wave signal, that is passed to control circuit 380. The R-wave signals are also used by control circuit 380 for determining ventricular intervals, referred to as "RR intervals" or "RRIs" for detecting tachyarrhythmia and determining a need for therapy. A ventricular interval or RRI is the time interval between two consecutively sensed R-waves and may be determined between two consecutive R-wave signals received from sensing circuit 386. For example, control circuit 380 may include a timing circuit 390 for determining RRIs between consecutive R-wave signals received from sensing circuit 386 and for controlling various timers and/or counters used to control the timing of therapy delivery by therapy delivery circuit 384. Timing circuit 390 may additionally set time windows such as morphology template windows, morphology analysis windows or perform other timing related functions of ICD 314 including synchronizing CV/DF shocks or other therapies delivered by therapy delivery circuit 384 with sensed R-waves.

Tachyarrhythmia detector 392 is configured to analyze signals received from sensing circuit 386 for detecting tachyarrhythmia episodes. Tachyarrhythmia detector 392 may be implemented in control circuit 380 as software, hardware and/or firmware that processes and analyzes signals received from sensing circuit 386 for detecting VT and/or VF. In some examples, tachyarrhythmia detector 392 may include comparators and counters for counting RRIs determined by timing circuit 390 that fall into various rate detection zones for determining a ventricular rate or performing other rate- or interval-based assessments for detecting and discriminating VT and VF. For example, tachyarrhythmia detector 392 may compare the RRIs determined by timing circuit 390 to one or more tachyarrhythmia detection interval zones, such as a tachycardia detection interval zone and a fibrillation detection interval zone. RRIs falling into a detection interval zone are counted by a respective VT interval counter or VF interval counter and in some cases in a combined VT/VF interval counter included in tachyarrhythmia detector 392.

When a VT or VF interval counter reaches a threshold count value, referred to as "number of intervals to detect" or "NID," a ventricular tachyarrhythmia may be detected by control circuit 380. Tachyarrhythmia detector 392 may be configured to perform other signal analysis for determining if other detection criteria are satisfied before detecting VT or VF when an NID is reached. For example, cardiac signal analysis may be performed to determine if R-wave morphology criteria, onset criteria, and noise and oversensing rejection criteria are satisfied in order to determine if the VT/VF detection should be made or withheld.

In instances in which ICD 314 is co-implanted with VAD 100, ICD 314 may be configured into a particular mode in which ICD 314 modifies its detection algorithm and/or therapy regimen based on communication with VAD 100. When configured into the particular detection mode that may utilize information from VAD 100, tachyarrhythmia detector 392 may withhold or delay the VT or VF detection if a communication signal from VAD 100 does not indicate a low flow condition. The low flow condition may, for example, be associated with the inability for the heart to adequately pump blood due to the VT or VF and thus be a confirmation of the detected VT or VF. Control circuit 380 may withhold or delay a therapy delivered by therapy delivery circuit 384 when tachyarrhythmia detector 392 detects VT or VF but a communication signal from VAD 100 does not indicate a low flow condition. On the other hand, control circuit 380 may respond to a communication signal from VAD 100 that does indicate a low flow condition by adjusting VT and/or VF detection criteria and/or confirming a detected VT or VF and advancing to therapy delivery by therapy delivery circuit 384. In other instances, tachyarrhythmia detector 392 may withhold or delay the VT or VF detection if no communication signal from VAD 100 indicating a low flow condition has been received prior to or within a threshold period of time after the VT or VF is detected by the ICD.

To support additional cardiac signal analyses performed by tachyarrhythmia detector 392, sensing circuit 386 may pass a digitized cardiac electrical signal to control circuit 380. A cardiac electrical signal from the selected sensing channel, e.g., from first sensing channel 383 and/or the second sensing channel 385, may be passed through a filter and amplifier, provided to a multiplexer and thereafter converted to multi-bit digital signals by an analog-to-digital converter, all included in sensing circuit 386, for storage in memory 382. Additional signal analyses may include morphological analysis of pre-determined time segments of the cardiac electrical signals or QRS waveforms.

In some examples, additional analysis may be performed to detect myocardial ischemia based on changes in the T-wave of a ventricular electrical signal, such as changes in T-wave amplitude, polarity, Q-T interval, or the like. For example, in response to a communication signal from VAD 100 indicating a low flow condition, ICD 314 may be configured to perform myocardial ischemia detection analysis of the ventricular electrical signal received by sensing circuit 386 for detecting and confirming myocardial ischemia and responding by generating an alert and/or adjusting a therapy. In some instances, the device may be a device other than an ICD, such as an insertable or wearable cardiac monitoring device with no therapy capabilities.

Therapy delivery circuit 384 includes charging circuitry, one or more charge storage devices such as one or more high voltage capacitors and/or low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 384 according to control signals received from control circuit 380. Timing circuit 390 of control circuit 380 may include various timers or counters that control when ATP or other cardiac pacing pulses are delivered. For example, timing circuit 390 may include programmable digital counters set by a microprocessor of the control circuit 380 for controlling the basic pacing time intervals associated with various pacing modes or ATP sequences delivered by ICD 314. The microprocessor of control circuit 380 may also set the amplitude, pulse width, polarity or other characteristics of the cardiac pacing pulses, which may be based on programmed values stored in memory 382.

In response to detecting VT or VF, control circuit 380 may control therapy delivery circuit 384 to deliver therapies such as ATP and/or CV/DF therapy. Therapy can be delivered by initiating charging of high voltage capacitors via a charging circuit, both included in therapy delivery circuit 384. Charging is controlled by control circuit 380, which monitors the voltage on the high voltage capacitors passed to control circuit 380 via a charging control line. When the voltage reaches a predetermined value set by control circuit 380, a logic signal is generated on a capacitor full line and passed to therapy delivery circuit 384, terminating charging. A CV/DF pulse is delivered to the heart under the control of the timing circuit 390 by an output circuit of therapy delivery circuit 384 via a control bus. The output circuit may include an output capacitor through which the charged high voltage capacitor is discharged via switching circuitry, e.g., an H-bridge, which determines the electrodes used for delivering the cardioversion or defibrillation pulse and the pulse wave shape. In some examples, the high voltage therapy circuit configured to deliver CV/DF shock pulses can be controlled by control circuit 380 to deliver pacing pulses, e.g., for delivering ATP or post shock pacing pulses. In other examples, therapy delivery circuit 384 may include a low voltage therapy circuit for generating and delivering relatively lower voltage pacing pulses for a variety of pacing needs.

Control parameters utilized by control circuit 380 for detecting cardiac arrhythmias and controlling therapy delivery may be programmed into memory 382 via telemetry circuit 388. Telemetry circuit 388 may include a transceiver and antenna for communicating with external device 40 (shown in FIG. 1A) using RF communication as described above. Under the control of control circuit 380, telemetry circuit 388 may receive downlink telemetry from and send uplink telemetry to external device 40.

Telemetry circuit 388 may be used to transmit and/or receive communication signals to/from another medical device implanted in patient 12, such as VAD 100. VAD 100 and ICD 314 may be configured to communicate via wireless RF communication though other communication techniques may be used.

Figure 4:
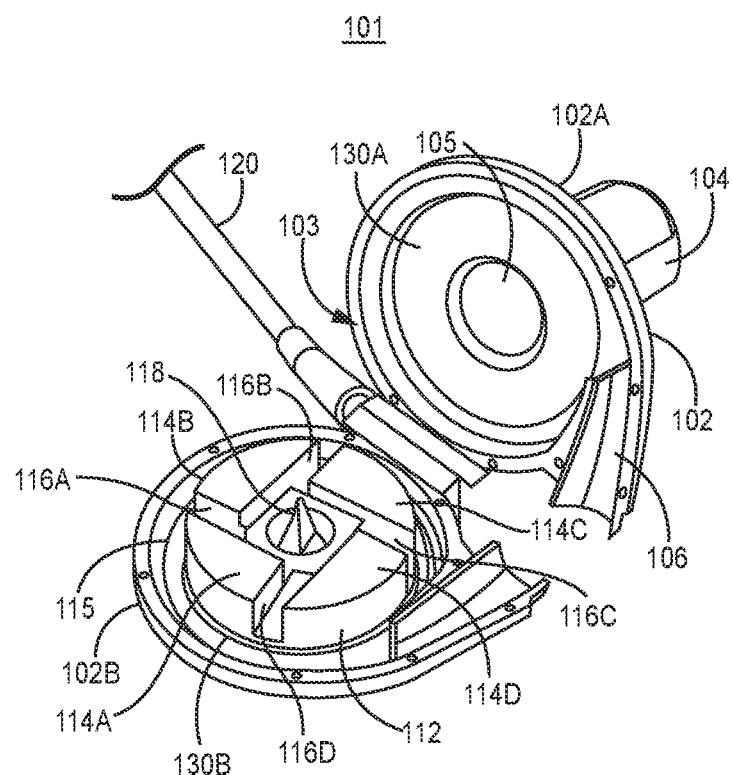
FIG. 4 is a conceptual, open diagram of the blood pump of the VAD shown in FIGS. 1A, 1B and 2.

FIG. 4 is a conceptual, open diagram of blood pump 101. Pump housing 102 may be a clam shell design having an upper portion 102a and a lower portion 102b (collectively pump housing 102) that are hermetically sealed upon closure to define an interior pump chamber 103. The inflow cannula 104 may be integrated with the pump housing 102 and defines an open lumen 105 as an axial inlet in fluid communication with the interior pump chamber 103. The open lumen 105 of inflow cannula 104 may be co-axial with a center post 118 that directs flowing blood entering pump housing 102 radially outward. Center post 118 may be co-axial with a center axis of the pump housing 102 and a rotating impeller 112. Impeller 112 may include multiple blades 114a-d defining open channels 116a-d extending in a generally radial direction from center post 118, between impeller blades 114a-d, to a circumferential open channel 115. Circumferential open channel 115 is in fluid communication with flow outlet 106, which extends tangentially along a peripheral portion of pump housing 102.

Impeller 112 may be the sole moving part within housing 102 and may be a unitary part defining blades 114a-d and channels 116a-d. As impeller 112 rotates, blades 114a-d push blood through the pump housing 102. Hydrodynamic and centrifugal force produced by the rotating impeller 112 produce a pressure difference, sometimes referred to as "pump head," between the inflow cannula 104 and the flow outlet 106, such that blood is moved from the inflow cannula 104 through the flow outlet 106 and vascular graft 108 (shown in FIG. 2).

Pump housing 102 is coupled to drive line 120 which delivers current to blood pump 101. An electromagnetic motor may be incorporated in pump housing 102 including one or more fixed electromagnetic stators 130a and 130b, collectively 130, and rotatable impeller 112. Fixed electromagnetic stators 130a and 130b may be incorporated in the respective upper portion 102a and/or lower portion 102b of pump housing 102, adjacent to the interior pump chamber 103 and rotatable impeller 112. Each electromagnetic stator 130a and 130b may include a plurality of electrical coils or windings arranged on a substantially circular iron core member for efficient electromagnetic coupling with corresponding magnetic regions of impeller 112 to cause rotation of impeller 112 within pump chamber 103. Each electromagnetic stator 130a and 130b is co-axial with the rotational axis of the impeller 112 and inflow cannula 104. The impeller 112 and each motor stator 130a and 130b may be substantially circular in horizontal cross section and may have substantially the same diameter to aid in radial stiffness of the rotating impeller during operation of blood pump 101. Electrical power is delivered to the coil windings of electromagnetic stators 130 by power cables carried within drive line 120. Drive line 120 may be a multi-lumen cable with each lumen carrying a power cable extending to each coil winding of stators 130a and 130b.

Impeller 112 includes one or more magnetic regions and may be radially and axially suspended in rotation by the magnetic forces produced by passive and active sources of magnetic flux acting upon impeller 112 by stators 130. Impeller 112 may be formed from a solid ferromagnetic or ferrimagnetic substance, such as a compression bonded neodymium, a platinum-cobalt alloy, or Alnico (aluminum-nickel alloy) and may be coated with a conformal polymer, such as Parylene, silicone or other biocompatible polymer, to prevent oxidation by hermetically sealing the ferromagnetic material of impeller 112. The conformal polymer coating may be covered by a hard, smooth outer coating to protect against wear and abrasion. Such coatings may include chromium nitride, or titanium-nitride. If the ferromagnetic substance of impeller 112 is biocompatible, such as a platinum-cobalt alloy, a protective surface coating may be optional. In other examples, impeller blades 114a-d may be formed as hollow casings formed of a biocompatible material, such as titanium or titanium alloy with each casing enclosing an internal permanent magnet housed within the hollow, hermetically sealed cavity of each blade.

The outer peripheral side wall of each of the blades 114a-b is convex in the radial direction with a radius of curvature that corresponds to the overall circular circumference of impeller 112. Each blade 114a-d may be defined by top and bottom planar surfaces separated by two opposing inner side walls, which may have rounded corners that define intervening channels 116a-d extending from center post 118 to circumferential open channel 115. The side walls of channels 116a-d extend inwardly from the convex peripheral side wall of each blade such that channels 116a-d may intersect at an angle of approximately 90 degrees near center post 118. The impeller blades 114a-d may be symmetrical. The impeller 112 has an open center lumen through which center post 118 extends thereby defining an axial blood flow passage between the upper and lower portions 102a and 102b of pump housing 102. All corners and edges of blood contacting surfaces within interior pump chamber 103 may be rounded to minimize thrombosis and hemolysis.

The impeller blades 114a-d may be magnetized to interact with magnetic forces imposed by the stators 130 to cause rotation of impeller 112 within the pumping chamber. The impeller 112 may be magnetically and hydrodynamically suspended from contact with the pump housing interior walls both radially and axially when the pump 101 is operating. Hydrodynamic bearing surfaces may produce axial thrust forces acting in one direction or axially opposite directions during operation of the pump 101 to suspend impeller 112 in an axial direction. Features and operation of blood pump 101 may correspond to the centrifugal blood pump generally disclosed in U.S. Pat. No. 7,976,271 (LaRose, et al.), incorporated herein by reference in its entirety. As a result of magnetic forces (a magnetic flux field) acting on impeller 112, impeller 112 is dynamically suspended between the upper and lower portions 102a and 102b of the pump housing 102 and rotates to move blood through the interior pump chamber 103, from inflow cannula 104 to flow outlet 106. The magnetic forces may be provided by permanent magnets, by electromagnetic circuits or by a combination of both.

Figure 5:
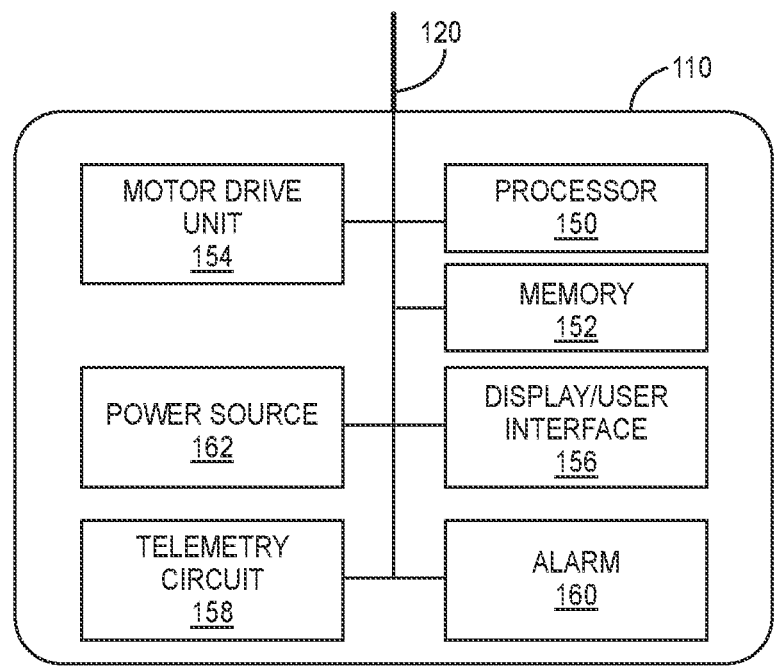
FIG. 5 is a conceptual diagram of the controller of the VAD shown in FIGS. 1A-2.

FIG. 5 is a conceptual diagram of controller 110 of VAD 100. Controller 110 may include a processor 150, memory 152, motor drive unit 154, display and user interface 156, telemetry circuit 158 and alarm 160. Controller 110 is coupled to drive line 120 for providing a drive current signal generated by motor drive unit 154 to the electromagnetic stators 130 of blood pump 101. Processor 150 may pass control signals to motor drive unit 154 to control the drive current signal and thereby control the rotational speed of impeller 112.

Power source 162 powers processor 150, memory 152, display and user interface 152, telemetry circuit 158, and alarm 160 and provides power to motor drive unit 154 needed to generate a current signal for driving blood pump 101. Power source 162 may include one or more of an AC power connection, DC power connection, and/or one or more batteries, which may include rechargeable and/or non-rechargeable batteries. In one example, power source 162 includes at least two, redundant power sources, such as two rechargeable batteries or a combination of an AC or DC power connection and one rechargeable battery to promote having a back-up power supply always available.

Processor 150 may be configured to estimate the blood flow rate of blood pump 101 based on electrical current of the drive signal, impeller rotational speed, and blood viscosity. Impeller speed may be estimated based on the back electromotive force (EMF) generated by the motor of blood pump 101. Drive line 120 may provide a back EMF signal to processor 150 from which the rotational speed of impeller 112 may be estimated. Blood viscosity may be calculated based on a nominal blood hematocrit stored in controller memory 152 or the patient's own hematocrit level entered into controller 110 by a user. Determination of estimated flow rate of blood pump 101 may be performed according to the techniques generally disclosed in U.S. Pat. No. 8,961,390 (LaRose), incorporated herein by reference in its entirety.

Processor 150 may be configured to estimate an instantaneous flow rate, e.g., as frequently as every 10 milliseconds, to generate an estimated flow rate waveform. Aspects of the estimated flow rate waveform may be used for detecting cardiac events, e.g., detecting a shockable rhythm event, a low flow event, or a suction event as described below in conjunction with the flow charts presented herein. A suction event can occur if the rotational speed of the impeller 112 is set too high for the flow input received from the heart. VAD 100 may attempt to pump a higher volume of blood than the flow input volume resulting in suction at the inflow cannula 104. Suction may occur due to ventricular collapse or inflow occlusion. If the left ventricle collapses, reduced ventricular volume may further reduce the blood flow input received by VAD 100 from the patient's heart. Ventricular collapse may occur in the presence of an arrhythmia, compromised right ventricular function, hypovolemia, or other causes. Inflow occlusion may occur when the inflow cannula 104 becomes obstructed by heart tissue. In some cases, a transient inflow occlusion may occur as a result of patient posture or straining (e.g., Valsalva maneuver).

The maximum peaks, the minimum peaks, and or mean of the pump flow rate waveform estimated over a predetermined time interval, e.g., 2 seconds, 3 seconds, 5 seconds, 8 seconds, 10 seconds or other time interval, may be determined and used by processor 150 for detecting a hemodynamic cardiac event. For instance, processor 150 may be configured to detect a suction event in response to a decrease of the minimum peaks of the estimated flow rate waveform below a threshold over a time interval of at least 10 seconds.

In some examples, processor 150 may be configured to discriminate between types of low flow events based on the behavior of the estimated flow rate. For instance, processor 150 may be configured to detect a shockable rhythm event in response to a sudden and sustained decrease in median flow rate and/or peak maximum flow rate. A threshold decrease in the mean estimated flow rate that occurs within a predetermined time interval, e.g., within 5 seconds, and is sustained for at least 5 seconds may be detected as a shockable rhythm event. Criteria for detecting and discriminating between suction events and shockable rhythm events may be defined. In other examples, a generic low flow event may be detected based on a sustained drop in estimated flow rate without discrimination between a suction event and an event suspected to be a shockable rhythm causing hemodynamic compromise.

Other examples of criteria that processor 150 may apply to the estimated flow rate data, which may be accumulated in buffers of memory 152, for detecting cardiac events are described below. Processor 150 may control motor drive unit 154 to adjust the impeller rotational speed in response to detecting a cardiac event or to maintain a desired, steady state flow rate. In response to detecting a cardiac event, processor 150 may control alarm 160 to generate an auditory alert to the patient, control display/user interface 156 to generate a visual display alert or audible alarm, control motor drive unit 154 to adjust the impeller speed by adjusting the drive current signal delivered to the motor stators 130, and/or control telemetry circuit 158 to transmit a signal to ICD 314.

Controller telemetry circuit 158 is configured to communicate with the ICD telemetry circuit 388 (FIG. 3), e.g., using an RF telemetry link as described above. Communication between ICD 314 and VAD 100 enables cooperative monitoring and detection of cardiac events and therapy management as described in conjunction with the flow charts presented herein.

Figure 6:
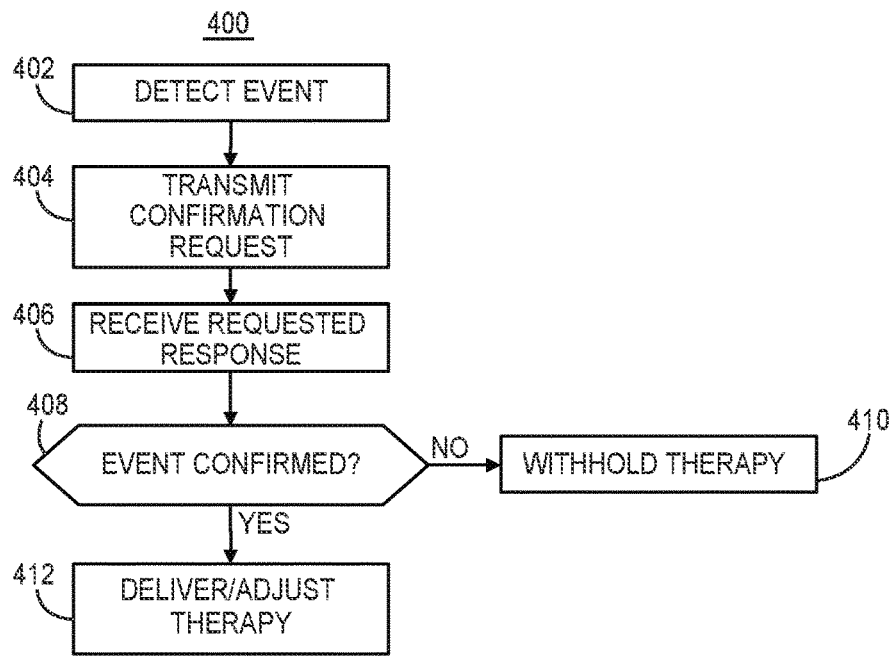
FIG. 6 is a flow chart of a method performed by a medical device system including an ICD and a VAD for detecting a cardiac event and managing therapy delivered to a patient by the medical device system.

FIG. 6 is a flow chart 400 of a method performed by the medical device system including ICD 314 and VAD 100 for managing therapy delivered to a patient by the system. At block 402, a cardiac event is detected. The cardiac event may be a cardiac arrhythmia detected by ICD 314 or a hemodynamic event detected by VAD 100 as examples. The cardiac event is detected by signal processing and analysis performed by the respective ICD 314 or VAD 100. For example, the event may be detected by ICD 314 based on tachyarrhythmia detection algorithms applied to cardiac electrical signals received from the patient's heart by ICD 314. In other instances, the event may be detected by VAD 100 based on event detection algorithms applied to an estimated blood pump flow rate determined by VAD processor 150. Upon detecting the cardiac event, the detecting device, either ICD 314 or VAD 100, transmits a communication signal at block 404 to the other, receiving device (to VAD 100 from ICD 314 or to ICD 314 from VAD 100) to request a confirmation signal of the detected event. The communication signal may, in some instances, trigger the receiving device to begin collecting and analyzing data to confirm the detected event. In other instances, the receiving device by be continuously monitoring for the detected event. The confirmation signal (or a non-confirmation signal) is generated by the receiving device based on signals monitored by the receiving device. The confirmation signal indicates that one or more signals monitored by the receiving device corroborate the event detected by the detecting device. Specific examples of detected events and confirmation by the other device are described below in conjunction with other flow charts presented herein. In other instances, ICD 314 and/or VAD 100 does not transmit a communication signal at block 404. Instead, VAD 100 and/or ICD 314 may be configured to automatically transmit an event detection signal to the other device in response to detecting the event. For example, VAD 100 may be configured to automatically transmit an event detection signal to ICD 314 in response to detecting low flow.

The detecting device receives the requested response signal at block 406, which is transmitted by the other one of the devices. The detecting device determines if the requested response signal received back from the receiving device corroborates the event detection and, if so, confirms the event detection at block 408. The detecting device selects a response to the detected cardiac event based at least in part on the response signal received from the receiving device. For example, if the detected cardiac event is confirmed based on a confirmation signal received back from the receiving device, the detecting device may deliver or adjust a therapy at block 412 or generate an alert or alarm.

If the requested response signal received back from the receiving device does not confirm or support the cardiac event detection, the detected event may not be confirmed at block 408. The detecting device may select a cardiac event response based on the received response signal, which may include withholding a therapy and/or a patient alert at block 410. The cardiac event detection may be deemed a false detection by the detecting device or an event that does not yet require therapy delivery. For instance, a proper tachycardia detection made by ICD 314 may not be a hemodynamically unstable tachycardia, based on a communication signal received from VAD 100 indicating that a low flow condition is not detected. As such, the detecting device may select a therapy response at block 410 by withholding or delaying therapy delivery in response to a requested signal transmitted back from the receiving device to the detecting device that does not corroborate the cardiac event detected by the detecting device. Further monitoring may be performed by one or both of ICD 314 and VAD 100 to continue or repeat the event detection until a therapy response is deemed appropriate or until event detection criteria applied by the detecting device are no longer satisfied.

Figure 7:
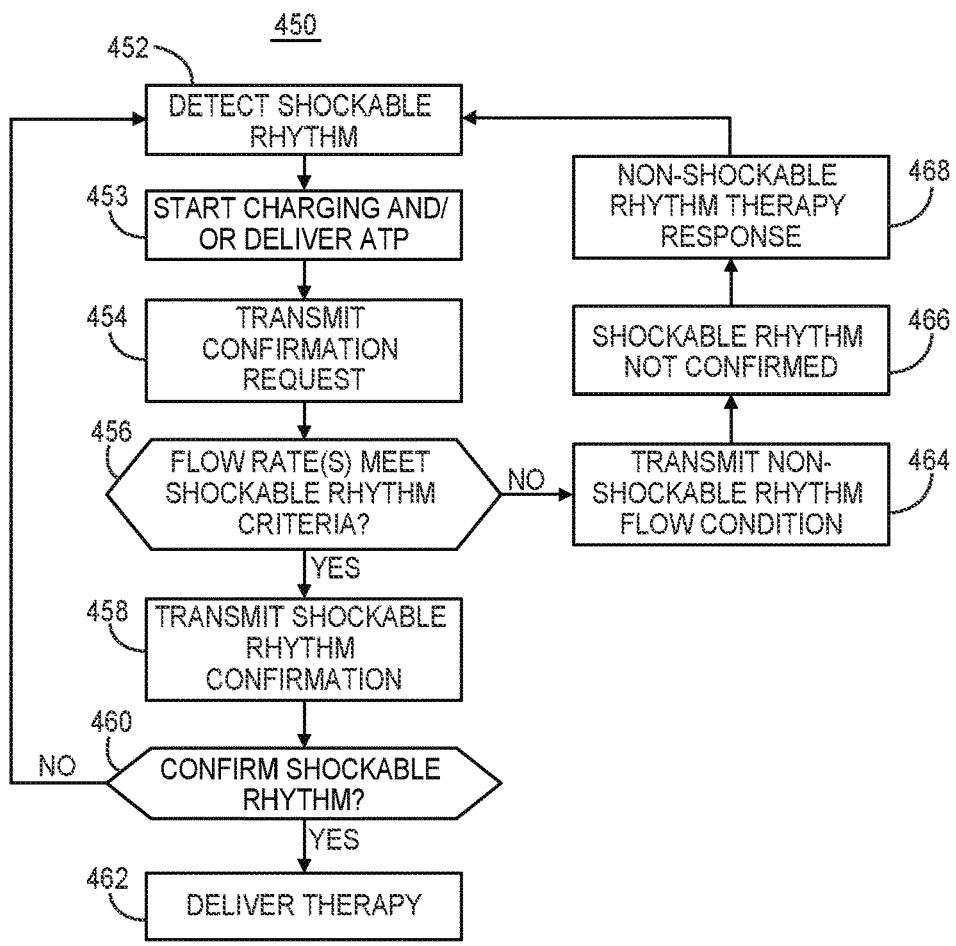
FIG. 7 is a flow chart of a method performed by a medical device system including an ICD and a VAD according to another example.

FIG. 7 is a flow chart 450 of a method performed by the medical device system including ICD 314 and VAD 100 according to another example. At block 452, ICD 314 detects a shockable rhythm from the cardiac electrical signal(s) received by sensing circuit 386. Control circuit 380 of ICD 314 may detect a shockable rhythm based on PP, PR, and/or RR intervals and/or cardiac electrical signal morphology. In some examples, ICD control circuit 380 may initiate charging of high voltage holding capacitors at block 453 upon detection of the shockable rhythm and continue charging during the subsequent process of waiting for a response from VAD 100 confirming presence of the event. In this way, any time delay in delivering a CV/DF shock is minimized if the requested signal from VAD 100 corroborates the shockable rhythm detection.

Additionally or alternatively, ICD control circuit 380 may control therapy delivery circuit 384 to deliver ATP therapy at block 453 in response to detecting the shockable rhythm based on the cardiac electrical signal. However, a CV/DF shock may not be delivered until after receiving a confirmation signal from VAD 100 verifying that the detected shockable rhythm is associated with a low flow condition warranting delivery of a shock therapy. In some cases, the shockable rhythm detected by ICD 314 may not cause clinically significant hemodynamic compromise in the presence of VAD 100. As such, unless VAD 100 confirms the detected shockable event based on estimated flow rate of blood pump 101, a CV/DF shock may be delayed or withheld. In some instances, ICD 314 only delays delivery of a CV/DF shock without receiving some sort of communication from VAD 100 for a particular period of time. For example, if no communication confirming or not confirming the cardiac event is received within 20 seconds of detecting the tachyarrhythmia, ICD may deliver the CV/DF shock.

In response to detecting the shockable rhythm at block 452, ICD control circuit 380 may control telemetry circuit 388 to transmit a confirmation request signal to VAD 100 at block 454. The signal may be transmitted as an RF signal via a RF transceiver in telemetry circuit 388. VAD 100 receives the transmitted request at block 456 and in response to the request compares estimated flow rate data to shockable rhythm confirmation criteria. VAD 100 may determine an updated flow rate estimate upon receiving the confirmation request. In some instances, one or more most recently determined flow rate estimate(s) may be available for use in comparing to shockable rhythm confirmation criteria so that an immediate comparison may be made without first determining an updated flow rate estimate.

In one example, the processor 150 determines an updated flow estimate and compares the updated flow rate estimate to a threshold rate. The threshold rate may be a programmed value stored by controller 110. The threshold rate may alternatively be a predetermined value determined by controller 110 as a percentage of a long term average flow rate. In another example, the threshold may be a percentage of a preceding estimated flow rate determined prior to receiving the confirmation request. For instance, a baseline flow rate may be established prior to receiving the confirmation request. In some examples a preceding estimated flow rate may be selected as a flow rate that was estimated at least a predetermined time interval earlier than receipt of the confirmation request in order to promote comparison of a current estimated flow rate to a preceding estimated flow rate that was most likely determined prior to the onset of the detected shockable rhythm episode. The shockable rhythm criteria compared to the current or most recent flow rate estimate is defined in order to promote detection of a drop in flow rate, both in magnitude and time course, which would be expected during VT or VF. Detection of such a drop in flow rate corroborates the detection of the shockable rhythm made by the ICD 314 and that a shock therapy is warranted.

If the estimated flow rate determined by VAD processor 150 meets shockable rhythm criteria, VAD 100 transmits a shockable flow condition signal as a shockable rhythm confirmation signal to ICD 314 at block 458. In some instances, VAD 100 may transmit the shockable flow condition signal without being triggered by ICD 314. Instead, VAD 100 may be configured to transmit the signal any time there is a low flow condition detected. At block 460, ICD 314 receives the shockable rhythm confirmation signal and confirms detection of the shockable rhythm. At block 462, ICD control circuit 380 controls therapy delivery circuit 384 to deliver therapy according to the type of rhythm detected and a programmed therapy delivery protocol. In some examples, a CV/DF shock is delivered at block 462 as soon as the shockable rhythm is confirmed and high voltage capacitor charging is complete. In other examples, ATP may be delivered upon confirming the shockable rhythm, which may occur during high voltage capacitor charging, in an attempt to terminate the shockable rhythm without requiring shock delivery.

In some examples, ATP is delivered at block 453 simultaneously with the communication with VAD 100. Upon receiving a shockable rhythm confirmation signal from VAD 100 at block 458, control circuit 380 may confirm the shockable rhythm detection at block 460 based on both the signal from VAD 100 and based on the shockable rhythm still being detected by control circuit 380 from the cardiac electrical signal(s) received by sensing circuit 382. If ATP is delivered simultaneously with communication with VAD 100, the ATP may successfully terminate the detected shockable rhythm. ICD control circuit 380 may determine that the shockable rhythm is not confirmed at block 460 if the shockable rhythm is no longer being detected from the cardiac electrical signal even if VAD 100 transmits a shockable rhythm confirmation signal at block 458 in some instances. ICD 314 may return to block 452 to wait for the next shockable rhythm detection.

If the shockable rhythm is confirmed at block 460 and therapy is delivered at block 462, ICD control circuit 380 may continue monitoring the cardiac electrical signal(s) for determining if the delivered therapy was successful in terminating the shockable rhythm or if the shockable rhythm is redetected. If redetection occurs, a confirmation request sent to VAD 100 is optional since the original episode detection has already been confirmed.

If the estimated flow rate determined by VAD processor 150 does not satisfy shockable rhythm criteria at block 456, VAD 100 may transmit a signal to ICD 314 indicating a non-shockable rhythm flow condition at block 464. The estimated flow rate may be an expected, normal flow rate, e.g., corresponding to normal sinus rhythm. The estimated flow rate may be a decreased flow rate but not below a threshold for confirming a shockable rhythm. For example, the estimated flow rate may be reduced due to a supraventricular tachyarrhythmia that reduces ventricular filling but is not deemed a shockable rhythm. In other instances, a relatively gradual decrease in flow rate that may begin earlier than the onset of the shockable rhythm episode detection may be indicative of a different issue than a shockable rhythm. As such, the shockable rhythm criteria may require that a threshold decrease in flow rate occurs within a defined time limit. In one example, the shockable rhythm criteria may require that a decrease between a first, earlier estimated flow rate and a second, later estimated flow rate meets a threshold negative slope, e.g., to indicate that a sudden drop in flow rate has occurred. In another example, an estimated flow rate less than a flow rate threshold may be required to occur within a predefined time interval before or after the shockable rhythm detection in order for the shockable rhythm criteria to be satisfied and/or may be required to remain below the flow rate threshold for at least a predetermined time interval. If shockable rhythm criteria are not met by the estimated flow rate signal determined and analyzed by VAD processor 150, a non-shockable rhythm flow condition signal is transmitted from VAD 100 to ICD 314 at block 464.

In response to receiving the non-shockable rhythm flow condition signal at block 464, ICD 314 does not confirm the shockable rhythm detection at block 466. ICD 314 may have properly detected a shockable rhythm from the cardiac electrical signal(s) received by sensing circuit 382, but the patient may not be hemodynamically compromised, particular with VAD support, such that an immediate shock may not be required. ICD 314 may withhold a CV/DF shock at block 468 that would normally be scheduled in response to the detected shockable rhythm. In some cases, all therapy is withheld in response to the non-shockable rhythm flow condition signal being received. In other examples, a non-shock therapy or an adjusted therapy may be delivered in response to not confirming the shockable rhythm detection. For example, overdrive ventricular pacing, CRT pacing, ATP, atrial overdrive pacing, or another pacing therapy may be delivered at block 468 in an attempt to regain or maintain a relatively stable hemodynamic state, e.g., if a reduced flow is detected but does not meet shockable rhythm criteria.

The ICD 314 may return to block 452 to continue monitoring the cardiac electrical signals to determine if the shockable rhythm continues to be detected by ICD 314 after withholding or adjusting therapy. Another confirmation request may be sent to VAD 100 if the shockable rhythm detection is sustained or redetection occurs after withholding or adjusting therapy at block 468. In this way, if the detected shockable rhythm does become hemodynamically unstable based on the estimated flow rate determined by VAD 100, a CV/DF shock may be delivered.

Figure 8:
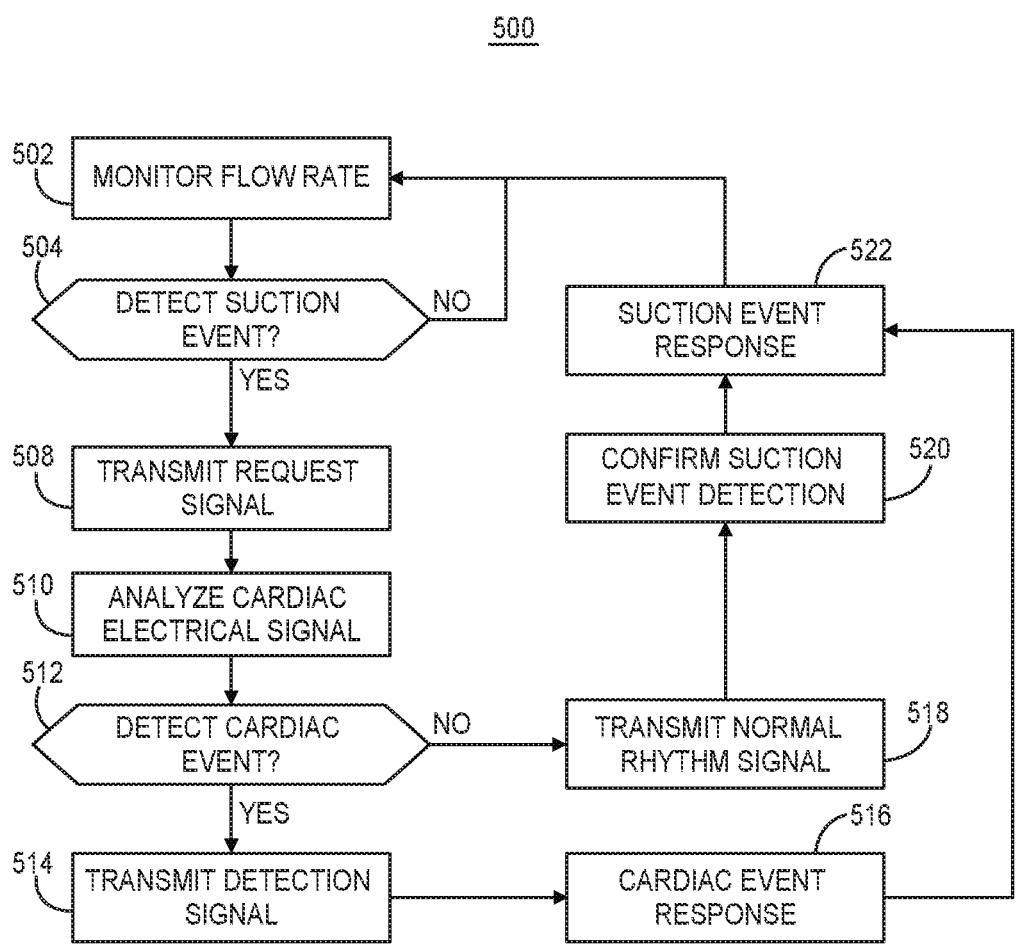
FIG. 8 is a flow chart of a method that may be performed by a medical device system including an ICD and VAD according to another example.

FIG. 8 is a flow chart 500 of a method that may be performed by the medical device system including ICD 314 and VAD 100 according to another example. In this example, VAD 100 may detect a suction event based on flow rate estimation and transmit a request to ICD 314 to confirm the detected event and/or alert ICD 314 to a decreased flow condition.

At block 502, VAD processor 150 determines an estimated flow rate signal and monitors the flow rate signal to detect a drop in flow rate. At block 504, VAD 100 compares the estimated flow rate signal to suction detection criteria to determine if the estimated flow rate meets suction detection criteria. Suction detection criteria may require that a minimum peak of the estimated flow waveform be less than a suction detection threshold for a predetermined time interval, e.g., 5 seconds, 10 seconds or more. In other examples, if a mean estimated flow rate or a negative slope of a decreasing mean estimated flow rate is less than a respective threshold, suction detection criteria may be satisfied.

In response to suction detection criteria being satisfied at block 504, VAD 100 transmits a request signal to ICD 314 at block 508. In response to receiving the request signal, ICD 314 analyzes the cardiac electrical signal(s) received by sensing circuit 382 for detecting a cardiac event at block 510. In some examples, the cardiac signal is analyzed according to an arrhythmia detection algorithm at block 510 in response to receiving the request signal. Additionally or alternatively, ICD control circuit 380 may analyze the cardiac electrical signal for detecting myocardial ischemia at block 510. In some cases, ICD 314 may already be in the process of detecting an abnormal heart rhythm at the time that the request signal is received. The decrease in the estimated flow rate that caused the suction event to be detected by VAD 100 may be caused by bradycardia or ventricular or supraventricular tachyarrhythmia.

If a cardiac rhythm event is detected by ICD 314, a notification signal is transmitted back to VAD 100 at block 514. ICD 314 may be configured to provide a cardiac event response at block 516. For instance, ICD 314 may detect an arrhythmia at block 512 based on the cardiac electrical signal analysis. In response, ICD 314 may transmit an arrhythmia detection signal back to VAD 100 at block 514. ICD 314 may continue to monitor the heart rhythm and/or deliver an appropriate therapy, such as bradycardia pacing, overdrive pacing, CRT, ATP, and/or CV/DF shock at block 516 according to detection and therapy delivery protocols implemented in ICD 314. The combination of the request signal received from VAD 100 and cardiac electrical signal analysis may lead to cardiac event detection and subsequent therapy delivery at block 516.

In other instances, ICD 314 may detect myocardial ischemia, e.g., based on a change in the T-wave and/or Q-T segment of the cardiac electrical signal analyzed at block 510. An ischemia detection signal may be transmitted back to VAD 100 at block 514, and an ischemia response may be provided at block 516, such as generating a patient or clinician alert signal by ICD control circuit 382.

In some examples, the medical device system provides a suction event response at block 522. The suction event response may be performed by one or both of VAD 100 and ICD 314. For example, VAD 100 may produce a patient alarm and/or store event data. ICD 314 may deliver a pacing therapy to alter the mechanical contractions of the heart in a manner that alleviates and corrects the suction event. In the case of a detected arrhythmia, the decrease in estimated flow rate that led to detecting the suction event may or may not have led to an actual suction event. The decreased flow rate may be due only to lower ventricular output due to the arrhythmia without ventricular collapse or inflow cannula occlusion. In other cases, the lower ventricular output due to an arrhythmia may also lead to an actual suction event. In both cases, a suction event response provided by VAD 100 at block 522 may be to store the estimated flow rate data resulting in the detected suction event in memory of controller 110 along with the receipt of the arrhythmia detection from ICD 314. Storing a history of low or reduced flow detections with a corresponding arrhythmia detection may provide diagnostic and prognostic data useful to a clinician in programming ICD 314, programming VAD 100 and overall patient management. Stored event detection data may be displayed on the display of controller 110 or transmitted to a clinician as an alert or notification.

In other examples, the suction event response at block 522 may include decreasing the drive signal to the motor of VAD 100 to reduce the impeller speed. The impeller speed may be gradually increased after a delay to allow an anti-arrhythmia therapy delivered by ICD 314 (at block 516) to promote a more normal rhythm to increase ventricular volume and/or output again to thereby increase the flow input to VAD 100. VAD 100 may continue monitoring the estimated flow rate at block 502. In some cases, the suction event response provided at block 522 may be dependent on magnitude of the decrease in estimated flow rate. A moderate decrease may indicate a decrease in flow due to an arrhythmia without an actual suction event, in which case an anti-arrhythmia electrical stimulation therapy delivered by ICD 314 may be the only response required. A sudden drop in minimum peak flow rate may indicate an actual suction event for which a change in the impeller speed and/or a patient alarm may be warranted.

If ICD 314 does not detect a cardiac event at block 512 based on cardiac electrical signal analysis at the time of receiving the request signal, ICD 314 may transmit a normal rhythm signal to VAD 100 at block 518. VAD 100 may confirm the non-arrhythmia related suction event detection at block 520 and provide a suction event response at block 522. The suction event response may include alarm generated by controller 110 and or an automatic change in impeller speed. A positional change, hypovolemia or other condition may have caused the suction event in the presence of a normal electrical rhythm of the heart. Even under normal rhythm conditions, however, ICD 314 may perform a suction event response at block 522 by delivering cardiac pacing to alter the mechanical contractions of the ventricles to correct the suction event.

Figure 9:
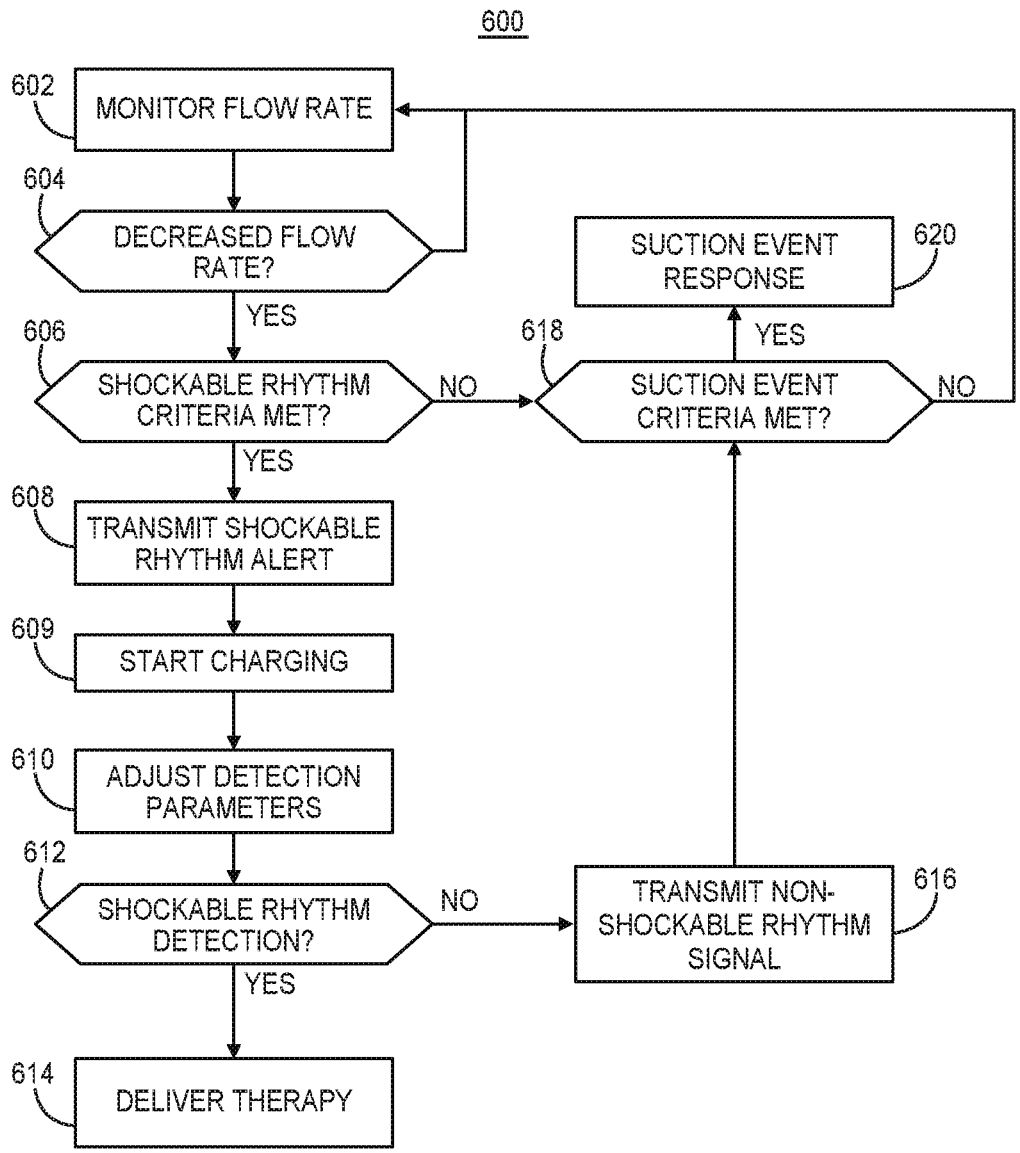
FIG. 9 is a flow chart of a method performed by a medical device system including an ICD and a VAD according to yet another example.

FIG. 9 is a flow chart 600 of a method performed by the medical device system including ICD 314 and VAD 100 according to another example. At block 602, VAD 100 monitors the estimated flow rate and compares estimated flow rate signal to decreased flow rate criteria at block 604. For example, a current estimated flow rate may be compared to a preceding estimated flow rate to determine if a decreasing trend is detected. A comparison between a current flow rate and a threshold, either predetermined and stored in memory 152 or based on a preceding flow rate estimate, may be performed to provide high sensitivity to detecting cardiac events. If no threshold decrease in estimated flow rate is detected, VAD 100 continues to monitor flow rate at block 602. After detecting a non-specific threshold decrease in flow rate, additional criteria may be applied to the estimated flow rate data for detecting and discriminating cardiac events that lead to a decreased flow rate with higher specificity.

For example, once a non-specific decrease in flow rate is detected at block 604, shockable rhythm criteria may be applied at block 606 to estimated flow rate data acquired before and/or after detecting the decreased flow rate. Shockable rhythm criteria applied to the estimated flow rate data may require that the estimated flow rate present a pattern consistent with a decrease in flow rate due to VT or VF. For example, the estimated flow rate may be required to continue to decrease for a predetermined time interval at a rate of decreasing flow that falls within a predetermined decreasing slope range. If shockable rhythm criteria are met at block 606, VAD 100 transmits a shockable rhythm alert to ICD 314 at block 608.

In some examples, ICD control circuit 380 may respond to a shockable rhythm alert received from VAD 100 by controlling therapy delivery circuit 384 to start high voltage capacitor charging at block 609 and/or by adjusting VT/VF detection parameters used by tachyarrhythmia detector 392 at block 610 to allow earlier detection of a shockable rhythm and/or early shock delivery. For example, the number of VT or VF intervals required to detect a shockable rhythm may be reduced at block 610. If VT and VF interval counters included in tachyarrhythmia detector 392 have already reached the adjusted threshold, an immediate shockable rhythm detection may be made by control circuit 380 at block 612 in response to the adjusted detection parameters being satisfied and the receipt of the shockable rhythm alert from VAD 100. If a shockable rhythm is detected, ICD control circuit 380 controls therapy delivery circuit 384 to deliver therapy at block 614. Therapy may include ATP prior to shock delivery which may be successful in terminating the shockable rhythm without requiring shock delivery. In other examples, a CV/DF shock is delivered at block 614 without being preceded by ATP. After delivering a first therapy attempt, ICD 314 continues to monitor the cardiac electrical signals received by sensing circuit 382 to determine if the shockable rhythm has been successfully terminated and, if not, delivery subsequent therapies according to a programmed therapy protocol at block 614.

Suction event criteria may be applied to estimated flow rate data at block 618 if shockable rhythm criteria applied to the flow rate data are not satisfied ("no" branch of block 606). If shockable rhythm criteria are satisfied at block 606 but a shockable rhythm is not detected by ICD 314 at block 612, using adjusted or non-adjusted detection parameters, ICD 314 may transmit a non-shockable rhythm signal to VAD 100 at block 616. VAD 100 determines if suction event criteria are met at block 618 in response to the non-shockable rhythm signal received back from ICD 314.

The flow chart 600 shows suction event criteria being applied at block 618 only if shockable rhythm criteria are not met ("no" branch of block 606) or a non-shockable rhythm signal is received from ICD 314 (block 616). It is to be understood, however, that the shockable rhythm criteria applied at block 606 and suction event criteria applied at block 618 may be applied to estimated flow rate data in parallel. VAD 100 may determine if suction event criteria are met whether shockable rhythm criteria are met or not. In some examples, if shockable rhythm criteria are met, VAD 100 may wait for ICD 314 to respond before taking further action as shown by the flow of FIG. 9. If a shockable rhythm is present, therapy delivered by ICD 314 may appropriately terminate the shockable rhythm and restore a normal flow rate. In other examples, however, VAD 100 may perform blocks 606 and 618 in parallel to detect a suction event even if a shockable rhythm is present since an arrhythmia may lead to a suction event.

In some examples, suction event criteria are defined differently than shockable rhythm criteria. For instance, a suction event caused by inflow cannula occlusion may occur suddenly, with a relatively large and sudden drop in the minimum peak of the estimated flow rate waveform. A flow decrease due to a shockable rhythm may also be a relatively sudden drop in flow rate but the maximum peaks of the flow waveform, minimum peaks of the flow waveform, mean flow rate, slope of the flow rate decrease or other aspects of the estimated flow rate signal may present a different pattern than the flow rate signal during an actual suction event. Differences in the behavior of the estimated flow rate waveform during a shockable rhythm and during an actual suction event may be used to define different suction event criteria and shockable rhythm criteria for discriminating the two events. If suction event criteria are met at block 618, a suction event response may be provided at block 620 by VAD 100 and may include generating an alarm by controller 110, transmitting an alert to a clinician, adjusting the impeller speed, and/or storing the event data in controller memory 152 for display to and review by a clinician.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, an system, including a cardiac stimulation device and a VAD for cooperatively monitoring for cardiac events and managing patient therapy, has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A system comprising:
    a blood pump comprising a motor, an inflow cannula for receiving blood from a patient's heart, and a flow outlet for coupling to a patient's artery;
    a controller comprising a power source, a processor and a telemetry circuit configured for communication with a second device; and
    a drive line coupled between the blood pump and the controller for transmitting a drive signal to the blood pump;
        wherein the controller is configured to:
            estimate a flow rate of the blood pump;
            detect a cardiac event from the estimated flow rate by:
                comparing the estimated flow rate to suction event criteria; and
                detecting a suction event in response to the suction event criteria being satisfied; and
            control the telemetry circuit to transmit a request signal to the second device in response to detecting the cardiac event.

2. The system of claim 1, wherein the controller is further configured to:
    detect the cardiac event by comparing the estimated flow rate to a low flow threshold;
    in response to the estimated flow rate being less than the low flow threshold, compare the estimated flow rate to shockable rhythm criteria; and
    transmit the request signal to the second device in response to the shockable rhythm criteria being met.

3. The system of claim 1, wherein the telemetry circuit is configured to receive a response signal from the second device, the response signal comprising one of:
    a normal rhythm signal; or
    an arrhythmia detection signal; and
    wherein the controller is configured to select a response to the detected cardiac event based on the response signal received from the second device.

4. The system of claim 3, wherein the controller withholds a response to the detected cardiac event based on the response signal received from the second device.

5. The system of claim 1, further comprising the second device, wherein the second device comprises:
    a sensing circuit configured to receive a cardiac electrical signal produced by a patient's heart;
    a therapy delivery circuit configured to deliver an electrical stimulation therapy to the patient's heart;
    a telemetry circuit configured for communication with the first device; and
    a control circuit coupled to the sensing circuit, the therapy delivery circuit and the telemetry circuit and configured to:
    adjust an arrhythmia detection parameter in response to receiving the request signal;
    detect an arrhythmia from the cardiac electrical signal received by the sensing circuit in response to the adjusted arrhythmia detection parameter being met.

6. The system of claim 5, wherein the second device control circuit is configured to control the therapy delivery circuit to deliver a therapy in response to detecting the arrhythmia.

7. The system of claim 1, further comprising the second device, wherein the second device is configured to:
    receive a cardiac electrical signal; and
    analyze the cardiac electrical for detecting myocardial ischemia in response to receiving the request signal.

8. The system of claim 7, wherein the system is configured to generate a patient alarm in response to the second device detecting the myocardial ischemia.

9. The system of claim 1, wherein the controller is configured to generate a patient alarm in response to detecting the cardiac event.

10. The system of claim 1, wherein the controller is configured to adjust a speed of the blood pump in response to detecting the cardiac event.

11. The system of claim 1, further comprising the second device, the second device comprising:
 a sensing circuit configured to receive a cardiac electrical signal produced by a patient's heart;
 a therapy delivery circuit configured to deliver an electrical stimulation therapy to the patient's heart;
a telemetry circuit configured for bidirectional communication with the first device; and
 a control circuit coupled to the sensing circuit, the therapy delivery circuit and the telemetry circuit and configured to control the therapy delivery circuit to deliver the electrical stimulation therapy in response to receiving the request signal.

12. A method comprising:
 estimating a flow rate of a blood pump;
 comparing the estimated flow rate to a low flow threshold;
 determining that the estimated flow rate is less than the low flow threshold;
 in response to the estimated flow rate being less than the low flow threshold, detecting a cardiac event from the estimated flow rate by at least one of:
  i) comparing the estimated flow rate to suction event criteria; or
  ii) comparing the estimated flow rate to shockable rhythm criteria; and
 transmitting a request signal to a second device in response to detecting the cardiac event.

13. The method of claim 12, wherein detecting the cardiac event comprises
 detecting a suction event in response to the suction event criteria being satisfied.

14. The method of claim 12, wherein detecting the cardiac event comprises
 detecting a shockable rhythm in response to the shockable rhythm criteria being met, and
 wherein transmitting the request signal comprises transmitting the request signal to the second device in response to the shockable rhythm criteria being met.

15. The method of claim 12, further comprising:
 receiving a response signal from the second device, the response signal comprising one of:
 a normal rhythm signal; or
 an arrhythmia detection signal; and
 selecting a response to the detected cardiac event based on the response signal received from the second device.

16. The method of claim 15, wherein selecting the response to the detected cardiac event comprises withholding a response to the detected cardiac event based on the response signal received from the second device.

17. The method of claim 12, further comprising at least one of:
 generating a patient alarm in response to detecting the cardiac event; and/or
 adjusting a speed of the blood pump in response to detecting the cardiac event.

18. A non-transitory, computer readable medium comprising a set of instructions which, when executed by a processor of a medical device, cause the medical device to:
 estimate a flow rate of a blood pump;
 compare the estimated flow rate to a low flow threshold;
 in response to the estimated flow rate being less than the low flow threshold, compare the estimated flow rate to shockable rhythm criteria;
 detect a cardiac event from the estimated flow rate by detecting a shockable rhythm in response to the shockable rhythm criteria being met; and
 transmit a request signal to a second device in response to detecting the cardiac event.

* * * * *